US009339528B2

(12) United States Patent
Han et al.

(10) Patent No.: US 9,339,528 B2
(45) Date of Patent: May 17, 2016

(54) METHODS FOR TREATING EPITHELIUM TRAUMA OF THE INTESTINAL MUCOSA USING INTERLEUKIN-1 RECEPTOR ANTAGONIST

(75) Inventors: Wei Han, Shanghai (CN); Di Xiang, Shanghai (CN); Zhenqian Wu, Shanghai (CN)

(73) Assignee: GENERAL REGENERATIVES, LTD., Hong Kong (CN)

( * ) Notice: Subject to any disclaimer, the term of this patent is extended or adjusted under 35 U.S.C. 154(b) by 146 days.

(21) Appl. No.: 13/504,114

(22) PCT Filed: Oct. 26, 2010

(86) PCT No.: PCT/CN2010/078102
§ 371 (c)(1),
(2), (4) Date: Apr. 25, 2012

(87) PCT Pub. No.: WO2011/050709
PCT Pub. Date: May 5, 2011

(65) Prior Publication Data
US 2012/0322723 A1 Dec. 20, 2012

(30) Foreign Application Priority Data
Oct. 26, 2009 (CN) .......................... 2009 1 0308755

(51) Int. Cl.
*A61K 38/20* (2006.01)
*A61K 38/17* (2006.01)
*C07K 14/54* (2006.01)
(52) U.S. Cl.
CPC ......... *A61K 38/2006* (2013.01); *A61K 38/1709* (2013.01); *C07K 14/54* (2013.01)
(58) Field of Classification Search
CPC . A61K 38/2006; A61K 38/1709; C07K 14/54
See application file for complete search history.

(56) References Cited

U.S. PATENT DOCUMENTS

| | | | |
|---|---|---|---|
| 5,075,222 A | 12/1991 | Hannum et al. | |
| 5,739,282 A | 4/1998 | Colotta et al. | |
| 5,747,444 A | 5/1998 | Haskill et al. | |
| 5,858,355 A | 1/1999 | Glorioso et al. | |
| 5,863,769 A | 1/1999 | Young | |
| 5,922,573 A | 7/1999 | Boraschi et al. | |
| 6,054,559 A | 4/2000 | Young | |
| 6,096,728 A * | 8/2000 | Collins et al. | 514/62 |
| 6,541,623 B1 * | 4/2003 | Ford et al. | 536/24.3 |
| 6,599,873 B1 | 7/2003 | Sommer et al. | |
| 8,323,635 B2 * | 12/2012 | Han et al. | 424/85.2 |
| 2010/0040603 A1 | 2/2010 | Han et al. | |
| 2010/0080756 A1 | 4/2010 | Han et al. | |

FOREIGN PATENT DOCUMENTS

| | | |
|---|---|---|
| DE | 42 19 626 | 12/1993 |
| WO | WO-91/08285 | 6/1991 |
| WO | WO-91/17184 | 11/1991 |
| WO | WO-91/17249 | 11/1991 |
| WO | WO-92/16221 | 10/1992 |
| WO | WO-94/06457 | 3/1994 |
| WO | WO-94/20517 | 9/1994 |
| WO | WO-94/21235 | 9/1994 |
| WO | WO-94/21275 | 9/1994 |
| WO | WO-96/12022 | 4/1996 |
| WO | WO-97/28828 | 8/1997 |
| WO | WO-99/36541 | 7/1999 |
| WO | WO-99/51744 | 10/1999 |
| WO | WO-01/87328 A2 | 11/2001 |
| WO | WO-01/89549 | 11/2001 |
| WO | WO-02/36152 | 5/2002 |
| WO | WO2005/097195 | * 10/2005 |
| WO | WO-2006/094971 | 9/2006 |
| WO | WO-2006/110577 A2 | 10/2006 |
| WO | WO2009/062339 | * 5/2009 |

OTHER PUBLICATIONS

Mickle, J.E. et al. Genotype-phenotype relationships in cystic fibrosis. Medical Clinicls of North America, 2000, vol. 84(3), p. 597-607.*
Wells, J.A. Additivity of mutational effects in proteins. Biochemistry, 1990, vol. 29, No. 37, p. 8509-8517.*
Chinese Office Action received for Chinese Appl. No. 200780102187.4, issued Jan. 18, 2012.
Chudgar et al., "Recombinant Human Interleukin-1 Receptor Antagonist Protects Early Myeloid Progenitors in a Murine Model of Cyclophosphamide-Induced Myelotoxicity," Blood, vol. 85, No. 9, May 1, 1995, pp. 2393-2401.
Cohen et al., "Treatment of rheumatoid arthritis with anakinra, a recombinant human interleukin-I receptor antagonist, in combination with methotrexate," Arthritis & Rheumatism, vol. 46, No. 3, pp. 614-624, Mar. 2002.
Cohen, "The use of anakinra, an interleukin-1 receptor antagonist, in the treatment of rheumatoid arthritis," Rheum. Dis. Clin. N. Am., vol. 30, pp. 365-380, 2004.
Database Biosis (Online); Biosciences Information Service; Philadelphia, PA (1996); Jovcic, G., et al.; "The effect of IL-1 receptor antagonist on the proliferation of hematopoietic progenitor cells in regenerating bone marrow"; (Abstract only) Database Accession No. PREV199698827004 (2 pgs.).

(Continued)

*Primary Examiner* — Robert Landsman
*Assistant Examiner* — Bruce D Hissong
(74) *Attorney, Agent, or Firm* — Foley & Lardner LLP

(57) ABSTRACT

The invention provides a use of the interleukin-1 receptor antagonist protein for preparing a medicament for preventing or treating epithelium trauma of the intestinal mucosa, wherein the protein is selected from: (a) a protein having an amino acid sequence as shown in SEQ ID NO: 1; (b) a protein which has a sequence having at least 70% homology with the amino acid sequence in the (a) and has the effect of preventing or treating epithelium trauma of the intestinal mucosa. The invention also provides a pharmaceutical composition comprising the protein (a) or (b) as the active component.

7 Claims, 23 Drawing Sheets

(56) References Cited

OTHER PUBLICATIONS

Database Biosis (Online); Biosciences Information Service; Philadelphia, PA, (1996); Neta Ruth, et al.; "Contrasting Mechanisms of the myeloprotective effects of interleukin-1 against ionizing radiation and cytotoxic 5-fluorouracil"; (Abstract only) Database Accession No. PREV199699013367 (2 pgs.).

First Examination Report received for European Application No. 07816824.2, issued Mar. 12, 2012.

Furst, "Anakinra: Review of recombinant human interleukin-I receptor antagonist in the treatment of rheumatoid arthritis," Clinical Therapeutics, vol. 26, No. 12, pp. 1960-1975, 2004.

Han, W. et al., "Local signals in stem cell-based bone marrow regeneration," Cell Research, vol. 16, pp. 189-195, 2006.

International Search Report and Written Opinion received for PCT/CN2007/003215, dated Aug. 14, 2008.

Jinquan, T. et al., "CXC chemokine receptor 3 expression on CD34+ hematopoietic progenitors from human cord blood induced by granulocyte-macrophage colony-stimulating factor: chemotaxis and adhesion induced by its ligands, interferon γ-inducible protein 10 and monokine induced by interferon γ," Blood Journal, vol. 96, No. 4, pp. 1230-1238, Aug. 15, 2000.

Lazzeri, E. et al., CXCR3-binding Chemokines: Novel Multifunctional Therapeutic Targets, Current Drug Targets—Immune, Endocrine & Metabolic Disorders, vol. 5, pp. 109-118, 2005.

Liao, F. et al., "Human Mig Chemokine: Biochemical and Functional Characterization," J. Exp. Med., vol. 182, pp. 1301-1314, Nov. 1995.

Non-final Office Action received for U.S. Appl. No. 12/740,264, dated Apr. 23, 2012.

Notice of Allowance received for U.S. Appl. 12/740,264, dated Aug. 2, 2012.

Rollins, B.J., "Chemokines," Blood Journal, vol. 90, No. 3, pp. 909-928, 1997.

Ruehlmann, J. M. et al., "MIG (CXCL9) Chemokine Gene Therapy Combines with Antibody-Cytokine Fusion Protein to Suppress Growth and Dissemination of Murine Colon Carcinoma," Cancer Research, vol. 61, pp. 8498-8503, Dec. 1, 2001.

Supplementary European Search Report received for European Patent Application No. 07816824.2, dated Jul. 20, 2011.

Zhang, R. et al., "Combination of MIG (CXCL9) chemokine gene therapy with low-dose cisplatin improves therapeutic efficacy against murine carcinoma," Gene Therapy, vol. 13, pp. 1263-1271, 2006.

Extended Search Report received in European Patent Application No. 10826072.0 mailed Feb. 6, 2014 (16 pages).

Soares, Pedro Marcos G. et al., "Mucosite Intestinal Experimental Induzida Por 5-Fluorouracil: Papel De IL-1beta, IL-4, Paf E Avaliacao Das Alteracoes Da Motilidade Digestiva," (Jan. 2008), (142 pages), retrieved from the internet: http://www.repositorio.ufc.br/bitstream/riufc/3740/1/2008_tese_pmgsoares.pdf—English Translation of Title: "Experimental intestinal mucositis induced by 5-fluororacil: role of IL-1β, IL-4 and PAF and assessing changes in gastrointestinal motitlity" (Original document is secured foreign language document and can only be viewed on the internet at address above. An English translation of an Abstract is attached.).

Soares, Pedro Marcos G. et al., "Role of IL-4 and IL-1β On the Pathogenesis of 5-Fluorouracil (5-FU) Induced Intestinal Inflammation in Mice," Gastroenterology, (Apr. 2008), vol. 134, No. 4, pp. A220-A221.

Souza, Danielle G. et al., "IL-1-Driven Endogenous IL-10 Production Protects Against the Systemic and Local Acute Inflammatory Response Following Intestinal Reperfusion Injury," Jnl of Immunology, (May 2003), vol. 170, No. 9, pp. 4759-4766.

Xiang, Di et al., "Interleukin-1 Receptor Antagonis Attenuates Cyclophosphamide-induced Mucositis in a Murine Model," Cancer Chemotherapy and Pharmacology, (2011), vol. 67, No. 6, pp. 1445-1453.

* cited by examiner

METHODS FOR TREATING EPITHELIUM TRAUMA OF THE INTESTINAL MUCOSA USING INTERLEUKIN-1 RECEPTOR ANTAGONIST

CROSS REFERENCE TO RELATED APPLICATIONS

This application is the U.S. National Stage of PCT/CN2010/078102, filed Oct. 26, 2010, which claims priority to Chinese Patent Application No. 200910308755.7, filed Oct. 26, 2009, both of which are hereby incorporated by reference in their entirety.

FIELD OF THE INVENTION

The present invention relates to the use of biomedical field and pharmaceutical compositions, specifically the use of interleukin-1 receptor antagonist and its pharmaceutical compositions.

BACKGROUND OF THE INVENTION

The normal small intestinal mucosa is composed of the mucosal epithelium, lamina propria and muscularis mucosa. The mucosal epithelium is the mucosal surface, consisting of a single-layer columnar epithelial lining. It along with the lamina propria forms a finger-like projection called intestinal villus, and the epithelium of the roots of villus sinking into the lamina propria forms crypt. Original epithelial cells proliferate in the crypts and shift to the top of villus, and in the process transit to physiological maturity. Generally, epithelial cells up to the middle of villus are fully in function. The renewal of the small intestinal villus occurs when the old epithelial cells at the top of villus constantly fall off to the intestinal lumen, and the proliferative cells move up to the top. The small intestinal epithelium has a high turnover rate. Normal replacement of the whole mucosa takes 5-6 days in humans, indicating that the epithelium of the small intestine loses $2-5 \times 10^7$ cells in every minute.

When the intestinal mucosa is injured, the epithelial cells of intestinal mucosa begin to shrink, denature and shed, and the cell renewal slows down. Currently, the major protective measure on the intestinal mucosal injury is enteral nutrition, which provides the intestinal mucosal immune cells with adequate nutrition matrix through the nutrient solution. In recent years, immune-enhancing enteral nutrition with special nutrients such as glutamine and arginine is increasingly used in clinic. And these substances can stimulate the mucosal immune response, mediate cytokine production and release, reduce excessive inflammation response and promote mucosal repair (Li, Y., Z. Yu, F. Liu, et al. *Tumori* 2006(92): 396-401; Barasch, A., D. E. Peterson. *Oral Oncol* 2003(39): 91-100; Goncharova, G. I., V. G. Dorofeichuk, A. Z. Smolianskaia, et al. *Antibiot Khimioter* 1998(34):462-466). In addition, the *bifidobacterium* and Chinese herbal medicine are used in clinic to reduce chemotherapy-induced intestinal mucosal injury (Boerma, M., J. Wang, A. F. Burnett, et al. *Cancer Res* 2007(67):9501-9506). Cytokines and chemokines secreted by small intestinal mucosal epithelial cells play an important role in the stability of the small intestine function. More and more studies have focused on the application of these factors in chemotherapy-induced intestinal mucosal damage and repair. IL-11 significantly reduces the mice mucosal damage induced by radiotherapy and chemotherapy, and plays different effects on the mucosal cells before and after injury, thus protects the mucosa by reducing damage and promoting repair after injury (Gibson, R. J., D. M. Keefe, F. M. Thompson, et al. *Dig Dis Sci* 2002(47):2751-2757; Naugler, K. M., K. A. Baer, and M. J. Ropeleski. 2008 *Am J Physiol Gastrointest Liver Physiol*). Latest research results indicate that it plays effect through the MEK pathway (Kim, K. A., M. Kakitani, J. Zhao, et al. *Science* 2005(309):1256-1259). In 2005, Klm et al. found that human growth factor R-spondin 1 significantly promotes the proliferation of crypt epithelial cells leading to the coarsening and extending of the small intestine and large intestine, and reduces the cell damage, the incidence of diarrhea and weight loss caused by chemotherapeutic agent 5-fluorouracil (Kim, K. A., J. Zhao, et al. *Cell Cycle* 2006(5):23-26; Booth, D., J. D. Haley, A. M. Bruskin, et al. *Int J Cancer* 2005(86):53-59). TGF-133 inhibits the cell cycle of epithelial cells in the G0 or G1 phase to protect small intestine from chemotherapy (Farrell, C. L., J. V. Bready, K. L. Rex, et al. *Cancer Res* 1998(58):933-939). KGF is another factor that can promote proliferation and has chemoprotective effect on mucosal epithelial cells. And KGF used before chemotherapy can greatly improve the survival ratio of crypt cells (Gibson, R. J., J. M. Bowen, and D. M. Keefe. et al. *Int J Cancer* 2005(116):464-470; Dinarello. *Blood* 1996(87):2095-2147). However, the safety of these growth factors has not yet been completely confirmed. Thus some scholars believe that the growth factors could promote the growth of tumor cells with growth factor receptors, and therefore the application of these drugs is limited.

SUMMARY OF THE INVENTION

The purpose of the present invention is to overcome the deficiencies of existing technology, and to provide a use of interleukin-1 receptor antagonist (IL-1Ra) and its pharmaceutical compositions. The protein of the invention can prevent or treat epithelium trauma of the intestinal mucosa effectively, and can reduce the incidence of diarrhea and weight loss, improve the intestinal damage caused by chemotherapy.

In one aspect, the invention provides a use of the following protein (a) or (b) for preparing a medicament for preventing or treating epithelium trauma of the intestinal mucosa:

(a) a protein having an amino acid sequence as shown in SEQ ID NO: 1 (rhIL-1Ra);

(b) a protein which has a sequence having at least 70% homology with the amino acid sequence in the (a) and has the effect of preventing or treating epithelium trauma of the intestinal mucosa.

In certain embodiments, the epithelium trauma of the intestinal mucosa comprises the intestinal mucosal epithelial damage caused by ischemia, hypoxia, toxins, radiation or medicine.

In certain embodiments, the medicaments are chemotherapeutic agents, wherein the chemotherapeutic agents comprise alkylating agents, antimetabolite agents, antibiotics agents, plant-derived anticancer agents, hormones agents, metal complexes, or protein agents, of which prefers cyclophosphamide (CTX) or 5-fluorouracil (5-FU).

In certain embodiments, the protein (b) is a protein which has a sequence having at least 77% homology with the amino acid sequence in the (a) and has the effect of preventing or treating epithelium trauma of the intestinal mucosa.

In another aspect, the invention provides a pharmaceutical composition, comprising the protein (a) or (b) as the active component and pharmaceutically acceptable carrier or excipient:

(a) a protein comprising an amino acid sequence as shown in SEQ ID NO: 1;

(b) a protein which has a sequence having at least 70% homology with the amino acid sequence in the (a) and has the effect of preventing or treating epithelium trauma of the intestinal mucosa.

In certain embodiments, the protein (b) is a protein which has a sequence having at least 77% homology with the amino acid sequence in the (a) and has the effect of preventing or treating epithelium trauma of the intestinal mucosa.

In another aspect, the invention provides methods of the protein as the active component for preventing or treating epithelium trauma of the intestinal mucosa, which comprise the administration of effective amount of the protein (a) or (b).

In certain embodiments, the epithelium trauma of the intestinal mucosa is caused by chemotherapy. In this implementation, the methods comprise administration of the effective amount of the protein (a) or (b) before, after, and/or at the same time of chemotherapeutic agents.

Compared with the existing technology, the invention has the following beneficial effects: The invention provides a medicament which can promote the proliferation of the intestinal mucosal epithelial cells or prevent and/or treat epithelium trauma of the intestinal mucosa. The protein of the invention can prevent or treat epithelium trauma of the intestinal mucosa effectively, and can reduce the incidence of diarrhea and weight loss, improve the intestinal damage caused by chemotherapy. It has potential to be a new medicament preventing or treating the chemotherapy-induced mucosal damage, reducing the side effects during clinical tumor treatment.

DETAILED DESCRIPTION OF THE EMBODIMENTS

Figure 1:
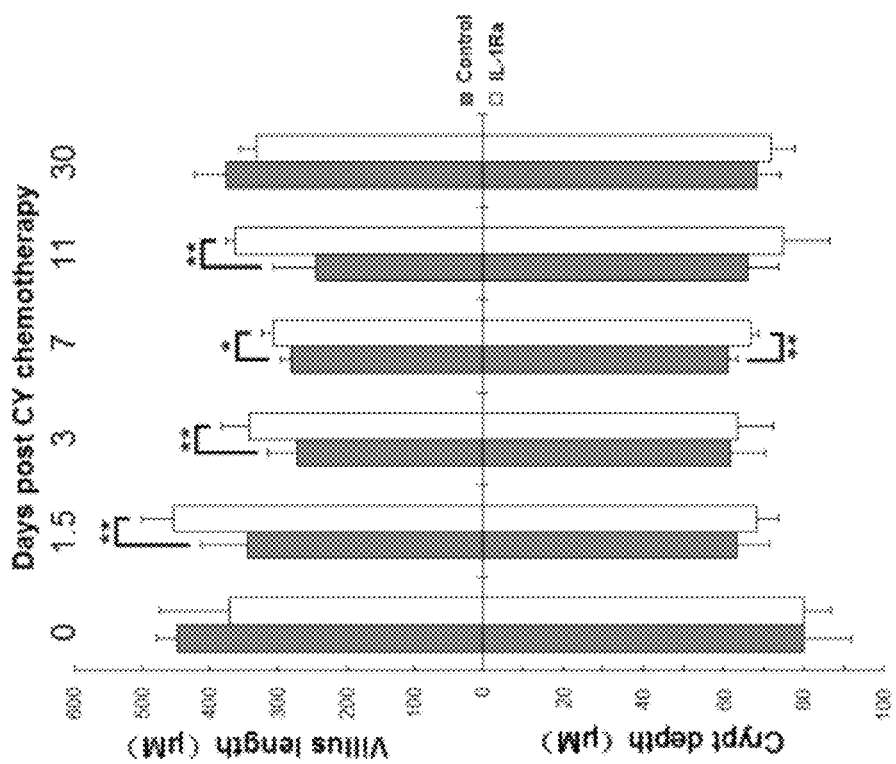
FIG. 1: The intestinal villus length of the mice that received preventive treatment of IL-1Ra before single dose cyclophosphamide chemotherapy.

The following embodiments will further describe the invention in connection with the figures. The embodiments give the detailed implementation and process which are based on the technical protocols of the invention. But the protection scope of the invention is not limited to the following embodiments. The experimental methods in the following embodiments which do not indicate the specific conditions are usually in accordance with the conventional conditions, or the manufacturer recommended conditions.

As used herein, the term "the disease of epithelium trauma of the intestinal mucosa" refers to the diseases caused by intestinal mucosal epithelial cell injury, death or proliferative retardation, comprising diarrhea, enteritis, intestinal damage-induced nutritional dysfunction and so on. Therefore, the invention also relates to the use of (a) a protein comprising an amino acid sequence as shown in SEQ ID NO: 1; or (b) a protein which has a sequence having at least 70% homology with the amino acid sequence in the (a) and has the effect of preventing or treating epithelium trauma of the intestinal mucosa, for preparing a medicament for preventing and/or treating diarrhea, enteritis, nutritional dysfunction caused by ischemia, hypoxia, toxins, radiation or medicine, especially the chemotherapeutic agents. The invention also involves the methods of preventing and/or treating diarrhea, enteritis, nutritional dysfunction caused by ischemia, hypoxia, toxins, radiation or medicine, especially the chemotherapeutic agents, which comprise the injection of protein (a) or (b) after ischemia or hypoxia, exposure to toxins or radiation, or before, after and/or at the same time of administering medicine such as chemotherapeutic agents.

"Interleukin-1 receptor antagonist" (IL-1Ra) is a member of IL-1 family, which also includes IL-1α and IL-1β. IL-1Ra is an antagonist of both IL-1α and IL-1β, and IL-1Ra has the similar protein sequence with IL-1α and IL-1β in the receptor binding site or the C-terminal region. The amino acid sequence of human interleukin-1 receptor antagonist (hIL-1Ra) as showed in SEQ ID NO: 1 has 77% homology with mouse IL-1Ra (amino acid sequence as shown in SEQ ID NO: 2), and the biological role of IL-1Ra is not species-specific. Therefore, the term "Interleukin-1 receptor antagonist" of the invention covers different species (e.g., from livestock (such as cattle, horses), pets (such as cats, dogs), primate animals, rodents (such as mice, rats)), most preferably human interleukin-1 receptor antagonist. Meanwhile, the term also covers the natural protein and the recombinant protein produced by bioengineering technology. The diversity of molecular weight of IL-1Ra from different cells is caused by different glycosylation. And it has been confirmed that glycosylation does not affect the biological activity of IL-1Ra (R Daig, G Rogler, E Aschenbrenner, et al. *Gut* 2000 (46):350-358).

As used herein, the term "interleukin-1 receptor antagonist" covers hIL-1Ra having an amino acid sequence as shown in SEQ ID NO: 1, its mutants, its functionally active fragments or derivates, and its homologous series with high degree of homology (e.g. orthologs).

The mutants or derivates refer to proteins with the same biological activity as hIL-1Ra, which could be the result of substituting, deleting or inserting one or multiple amino acids within the amino acid sequence indicated in SEQ ID NO: 1. For example, proteins derives from conservative substitution of amino acids ranging from 1 to 50, 1 to 25, 1 to 10 or 1 to 5 amino acids in the sequence, still featuring the same biological activity as hIL-1Ra, are referred to as such mutants and derivates. The mutants and derivates could also be proteins with the same biological activity as hIL-1Ra, which have at least 70% homology with the hIL-1Ra, preferably at least 75% homology, more preferably at least 80% homology, more preferably at least 85% homology, more preferably at least 90% homology, more preferably at least 95% homology, more preferably at least 96%, 97%, 98%, 99% homology.

The aforementioned derivates or mutants can be produced using known methods in the field of protein technology, comprising site-directed amino acid mutagenesis mediated by oligonucleotides, alanine scanning, PCR, etc. These derivates or mutants of hIL-1Ra can be produced through such processes to the cloned coding DNA, comprising site-directed mutagenesis (Carter et al. *Nucl. Acids Res.* 1986(13):4331; Zoller et al. *Nucl. Acids Res.* 1987(10):6487), cassette mutagenesis (Wells et al. *Gene* 1985(34):315), restriction selective mutagenesis (Wells et al, *Philos. Trans. R. Soc. London SerA* 1986(317):415) or other known techniques.

The "functionally active fragments" of the invention refer to proteins comprising at least 20, preferably 50, more preferably 100 continuous amino acids from the aforementioned amino acid sequence of hIL-1Ra, which have the same biological activity as hIL-1Ra.

The homologous percentage of proteins is determined by GAP (Needleman and Wunsh, 1970) analysis (GCG procedure), wherein the parameters: gap creation penalty=5, gap extension penalty=0.3. When the analyzed sequences are at the minimal 15 amino acids, the GAP analysis would be performed in regions of at least 15 amino acids between the two sequences in test. More preferably, when the analyzed sequences are at the minimal 50 amino acids, the GAP analysis would be performed in regions of at least 50 amino acids between the two sequences in test. More preferably, when the analyzed sequences are at the minimal 100 amino acids, the GAP analysis would be performed in regions of at least 100 amino acids between the two sequences in test. More preferably, when the analyzed sequences are at the minimal 250 amino acids, the GAP analysis would be performed in regions of at least 250 amino acids between the two sequences in test. Even more preferably, when the analyzed sequences are at the minimal 500 amino acids, the GAP analysis would be performed in regions of at least 500 amino acids between the two sequences in test.

The invention also relates to the protein analogues of IL-1Ra, which receive different modification during or after their synthesis, including biotinylation, benzylation, glycosylation, acetylation, phosphorylation, known protective/blocking group modification, cleavage using protein hydrolysis, connection to antibody molecules, connection to polymers or other cellular substances extending their in vivo half-life, and so on. These modifications can benefit the natural IL-1Ra with better physical or chemical performances like solubility, stability, bioavailability and/or half-life, etc. while maintaining its biological activity.

The Expression of the Protein

The present invention covers the DNA coding the present invention IL-1Ra, and the vectors and transformants containing such DNA.

As used herein, the term "transformant" refers to host cells carrying exogenous DNA molecules.

The present invention also covers the methods of producing proteins of the invention by techniques of synthesize and recombination. Polynucleotide (DNA or RNA), vectors, transformants and other organisms can be isolated and purified using known methods in this field.

The vectors used in the present invention may be phages, plasmids, cosmids, micro chromosomes, virus or retrovirus vectors. The vectors suitable for cloning and/or expressing the polynucleotide of the invention are those which could be utilized to replicate and/or express polynucleotide in host cells capable for replicating and/or expressing polynucleotide. Generally speaking, polynucleotide and/or vectors could be applied to any eukaryotic or prokaryotic cells, comprising mammalian cells (for example, human (e.g. Hela cells), monkey (e.g. Cos cells), rabbit (e.g. rabbit reticulocyte), rat, hamster (e.g. CHO, NSO and BHK), mouse (e.g. L cells)), plant cells, yeast cells, insect cells or bacterial cells (e.g. *E. coli*). The suitable vectors applicable to multiple host cells are referenced to F. Ausubel et al., *Current Protocols in Molecular Biology*, Greene Publishing Associates and Wiley-Interscience (1992) and Sambrook et al. (1989). These host cells carrying exogenous polynucleotides may be used to express proteins like drugs, diagnostic reagents, vaccines and therapeutic agents in large quantities.

Multiple techniques have been developed to connect polynucleotide to vectors through cohesive ends in a controlled manner. For example, complementary sequences may be added to DNA fragments which are to be inserted into vector DNAs. Inserting DNA and vector could thus be ligated to produce recombinant DNA molecules by the formation of hydrogen bonds between the complementary sequence tails.

Synthesized adaptors containing one or more restriction sites provide another method to connect DNA fragments and vectors. DNA fragments processed by restriction endonuclease are further treated with DNA polymerase of T4 DNA polymerase or DNA polymerase I from *E. coli*. These two polymerases excise the protruding γ-single strand terminal using their 3'-5' exonuclease activity, and then fill the 3' cohesive end using their polymerase activity. Thus, these combined activities result in blunt end DNA fragments. Then, with the existence of enzymes capable of catalyzing the interconnection between blunt end DNA molecules, for example, T4 DNA ligase, the blunt end fragments and excessive molar of adaptor molecules are incubated together. As the result, the product of such reaction is DNA fragments carrying adaptor sequences at both ends. These products are then processed with proper restriction enzymes, and connected to expressing vectors pre-treated with the same restriction enzymes capable of producing compatible ends to the DNA fragments on the vectors. Synthesized adaptors containing multiple restriction endonuclease sites could be purchased from multiple reagent merchants.

The polynucleotide insertion is connected to the appropriate promoters compatible with the host cells which express the polynucleotide. The promoters may be strong promoters and/or inducible promoters. Some examples of the promoters comprise the phage XPL promoter, $E.$ $coli$ lac, trP, phoA and tac promoter, SV40 early or late promoter, and retrovirus LTR promote. Other appropriate promoters are known to the technicians in this field. The recombinant expression vectors further comprise initiation sites and termination sites of transcription, and have the ribosome binding site for translation. The coding region of transcript expressed by recombinant vectors comprises translation initiation codon at the starting point and termination codon (UAA, UGA or UAG).

As mentioned above, the expression vectors may comprise at least one selective marker. The selective markers comprise dihydrofolate reductase, G418, glutamine synthase or neomycin resistance for culture of eukaryotic cells; and tetracycline, kanamycin or ampicillin resistance genes for culture of $E.$ $coli$ and other bacteria. Representative examples of the appropriate hosts include but are not limited to bacterial cells, such as $E.$ $coli,$ $streptomyces$ and $salmonella$ $typhimurium$ cells; fungal cells, such as yeast cells (e.g. wine yeast or $pichia$ $pastoris$ yeast); insect cells, such as $drosophila$ S2 cells and nocturnal moth SF9 cells; animal cells, such as CHO, COS, NSO, 293 and bowes melanoma cells; as well as plant cells. The appropriate medium and culture conditions of these host cells are known in the field.

To facilitate protein purification or secretion of target protein, tagged proteins or polypeptides (Tag) are usually used. Such Tags commonly used comprise glutathione S-transferase (GST), hexamer histidine peptide (His.Tag), protein A and cellulose binding domain. By the form of fusion proteins constituted by the special proteins (or peptides) and the target proteins, the characteristics of the tagged proteins or polypeptides could be used to isolate and purify the target proteins after expression, for example, the specific binding of His.Tag and Ni-Chelating Sepharose column. These purified tagged proteins or polypeptides may be digested and removed the fusion sequences by the site-specific proteases such as thrombin, enterokinase and factor Xa, and thus the target proteins are obtained.

The present invention also comprises the host cells containing the nucleotide sequence of the invention, and the nucleotide sequence may be connected with one or more heterologous control region (e.g. promoters and/or enhancer) using the known technology in this field. The host strain, which can regulate the expression of the inserted gene sequence or can modify the gene products using special ways needed, may be suitable for the present invention. With certain inducers, the expression driven by certain promoters may increase. Therefore, the expression of the peptide may be controlled by genetic modification. In addition, different host cells have characteristic and specific mechanism of protein translation, posttranslational processing and modification (e.g. phosphorylation and cleavage). Therefore, appropriate cell lines may be chosen to ensure a desirable modification and processing of the expressed exogenous protein.

Using calcium phosphate transfection, DEAE-dextran mediated transfection, cationic lipid-mediated transfection, electroporation, transduction, infection or other methods, the nucleic acids and their recombinant vectors of the present invention are imported into the host cells. These methods are described in many standard laboratory manuals, for example, Davis et al., $Basic$ $Methods$ $In$ $Molecular$ $Biology$ (1986).

The polynucleotide encoding the protein of the present invention may be cloned into the vectors containing selectable markers. The plasmid vector transduction may be mediated by calcium phosphate sediment or in the complexes with charged lipid. If the vectors are virus, they are packaged using appropriate packaging cells, and then transduced into the host cells.

Using the well-known technology, the successfully transformed cells containing the recombinant DNA vectors of the present invention can be identified. For example, the target peptides may be produced by the cultured cells containing the recombinant expression vectors. The cells may then be collected and lysed. Using the methods as described in the documents (Southern (1975) $J.$ $Mol.$ $Biol.$ 95, 503 or Berent et al. (1985) $Biotech.$ 3, 208), the presence of DNA of the present invention in the DNA preparation can be detected. Using the method of antibody, the presence of the target proteins in the supernatant can be detected.

It is more beneficial for using the well-known methods to recover and purify the protein of the present invention from the culture of recombinant cells. These methods comprise ammonium sulfate precipitation or ethanol precipitation, acid extraction, anion or cation exchange chromatography, phosphocellulose chromatography, hydrophobic chromatography, affinity chromatography, hydroxyapatite chromatography, hydrophobic charge chromatography and lectin chromatography. In certain embodiments, the method of high performance liquid chromatography (HPLC) can also be used to purify the protein of the present invention.

In certain embodiments, one or more chromatography methods described above can be used to purify the protein of the present invention. In other embodiments, one or more chromatography columns can be used to purify the protein of the present invention. These chromatography columns comprise Q Sepharose FF column, SP Sepharose FF column, Q Sepharose high performance column, Blue Sepharose column, Blue column, Phenyl Sepharose FF column, DEAE Sepharose FF column, Ni-Chelating Sepharose FF column or Methyl column, and so on.

In addition, the protein of the present invention can be purified using the method described in the patent (International publication number WO00/44772, the full text is listed in the present invention as a reference). And this method can be easily modified by technicians in this field to purify the protein of the present invention. The protein of the present invention can be recovered from the products of prokaryotic or eukaryotic hosts with recombination technology, and these hosts comprise the cells of bacteria, yeast, higher plant, insect and mammalian.

Composition

The present invention also relates to pharmaceutical compositions comprising the protein of the invention. Usually, when the compositions of the present invention are used for the above purposes, the protein of the invention can be mixed with one or more pharmaceutically acceptable carriers or excipients to product pharmaceutical dosage forms in different administration routes, and the pharmaceutical dosage forms comprise tablets, capsules, powders, granules, syrups, solutions, oral solutions, spiritus, tinctures, aerosols, powders of inhalations, injections, sterile powders of injection, suppositories, etc.

The "pharmaceutically acceptable" component means substances that can be applicable to human or animals without excessive adverse side effects (e.g. toxicity, irritation and allergy), that means having reasonable benefit/risk ratio. "The pharmaceutically acceptable carriers" mean pharmaceutical or food-acceptable solvent, suspending agent or excipient that can be used to transmit the protein of the invention to the animals or human. The carriers may be liquid or solid.

The routes of administration of the protein of the present invention comprise orally, intravenously, intramuscularly or subcutaneously.

In above formulations, the dosage forms of oral administration comprise: tablets, capsules, powders, granules, syrups, solution agents and spiritus. The solid-state carriers comprise: starch, lactose, calcium hydrogen phosphate, microcrystalline cellulose, sucrose, kaolin, silica powder, talcum powder, low-substituted hydroxypropyl cellulose, sodium carboxymethyl starch, polyvinyl pyrrolidone. And the liquid carriers comprise: sterile water, ethanol, polyethylene glycol, non-ionic surfactants and edible oils (e.g. corn oil, peanut oil and sesame oil). Adjuvants commonly used in the preparation of pharmaceutical compositions comprise: flavoring agents, coloring agents, preservatives (e.g. hydroxyl phenyl alkyl butyl, sodium benzoate and sorbic acid) and antioxidants (e.g. vitamin E, vitamin C, sodium metabisulfite and butylated hydroxyltoluene).

In above formulations, the dosage forms used for injection comprise: injection and sterile powder for injection, which are mixed by the medicament and one or more pharmaceutically acceptable excipients. The solutions comprise: sterile water, ethanol, glycerol, propylene glycol, polyethylene glycol. In addition, the injection may contain antibacterial agents (e.g. benzyl alcohol, hydroxyl benzene butyl, thimerosal), isotonic regulating agent (e.g. sodium chloride, glucose), suspending agents (e.g. sodium carboxymethyl cellulose, methyl cellulose), solubilizing agents (Tween-80, lecithin), antioxidants (e.g. vitamin E, vitamin C, sodium metabisulfite) and fillers (e.g. lactose, mannitol).

From the point of easy preparation and drug administration, the preferred pharmaceutical composition is a solid composition, especially the freeze-dried powder.

The pharmaceutical compositions of the present invention can be produced according to the methods of pharmaceutical production requirements that are well-known and recognized. The pharmaceutical compositions comprise the protein of the invention and pharmaceutically acceptable carriers, and suitable for unit dosage form. The pharmaceutical compositions of the present invention comprise the prodrug form of the protein of the invention. The prodrug could be metabolized into the active form in the body of the recipient.

The pharmaceutical compositions of the invention can also be combined with other therapies, such as simultaneous, sequential or separate application. The pharmaceutical compositions of the invention could comprise other active compounds.

Application

The present invention provides methods of the protein as the active component for preventing or treating epithelium trauma of the intestinal mucosa, which comprise the administration of effective amount of the protein (a) or (b).

Chemotherapeutic agents refer to drugs for the treatment of diseases caused by bacteria, fungus, viruses, parasites and malignant cells, abbreviated as chemotherapy drugs, which comprise antibacterial agents, antifungal agents, antiviral, antiparasitic and anticancer agents. Chemotherapeutic agents of the present invention are anticancer agents. According to their mechanism of action, they are divided into several categories:

1. Alkylating agents: alkylating agents can prevent cancer cell from replication by direct effect on DNA. These drugs treat chronic leukemia, malignant lymphoma, Hidgkin's disease, multiple myeloma, lung cancer, breast cancer and ovarian cancer. Alkylating agents mainly comprises busufan, cisplatin, cyclophosphamide, dacarbazine, ifosfamide, dichloromethane diethylamide and phenylalanine chlormethine.

2. Antimetabolites: antimetabolites interfering with DNA and RNA synthesis are for the treatment of chronic leukemia, breast cancer, ovarian cancer, gastric cancer and colorectal cancer. Antimetabolites mainly comprise 5-fluorouracil, methotrexate, cytarabine and cyclocylidine.

3. Antitumor antibiotics: antitumor antibiotics interfere with DNA by inhibiting the enzyme activities and mitosis or changing the cell membrane. Antitumor antibiotics are cell cycle non-specific drugs, widely used in cancer therapy. Antitumor antibiotics mainly comprise bleomycin, dactinomycin, rubidomycin, doxorubicin and biliflavin.

4. Plant-derived anticancer agents: plant-derived anticancer agents are alkaloids and natural products. They inhibit mitosis or the enzyme activities, preventing protein synthesis necessary for cell replication. Plant-derived anticancer agents are often used to treat multiple cancers together with other anticancer agents. Plant-derived anticancer agents mainly comprise vinblastine, vincristine, harringtonine, etoposide and vumon.

5. Others: some other chemotherapy agents have different mechanisms of action, not belong to the above categories, wherein comprising asparaginase and retinoic acid.

6. Hormones: corticosteroids are for the treatment of lymphoma, leukemia, multiple myeloma, and other cancers. When hormones are used to kill cancer cells or slow down the growth of cancer cells, they are regarded as chemotherapeutic agents. Corticosteroids comprise prednisone and dexamethasone. Sex hormones which comprise estrogen, antiestrogen, progesterone and male hormone, are used to slow down the growth of breast cancer, prostate cancer and endometrial cancer. The role of sex hormones is different from cytotoxic drugs, belonging to the special chemotherapy areas.

7. Immune agents: immune agents can stimulate the immune system of cancer patients to identify and attack cancer cells more effectively, belonging to the special chemotherapy areas.

The terms "Effective amount" or "treatment amount" is a quantity sufficient to achieve a desired therapeutic effect. The effective amount can be divided into one or multiple administration. Generally, effective amount could ease, improve, stabilize, slow down or delay further development of the diseases.

For the prevention or treatment of diseases mentioned above, the suitable amount of the IL-1Ra protein of the present invention will depend on the type of disease, severity and development of disease, use for prevention or treatment, as well as the subjective judgment of the physician. The effective amount of the used active compositions may be changed with the pattern of administration and the severity of disease. For most large mammals, the daily total amount is about 0.01-1000 mg. Usually, adult clinical amount is about 0.01-200 mg/day, preferably 0.05-100 mg/day. Generally, an effective amount of drug is determined by the standard method of the field.

Figure 20:
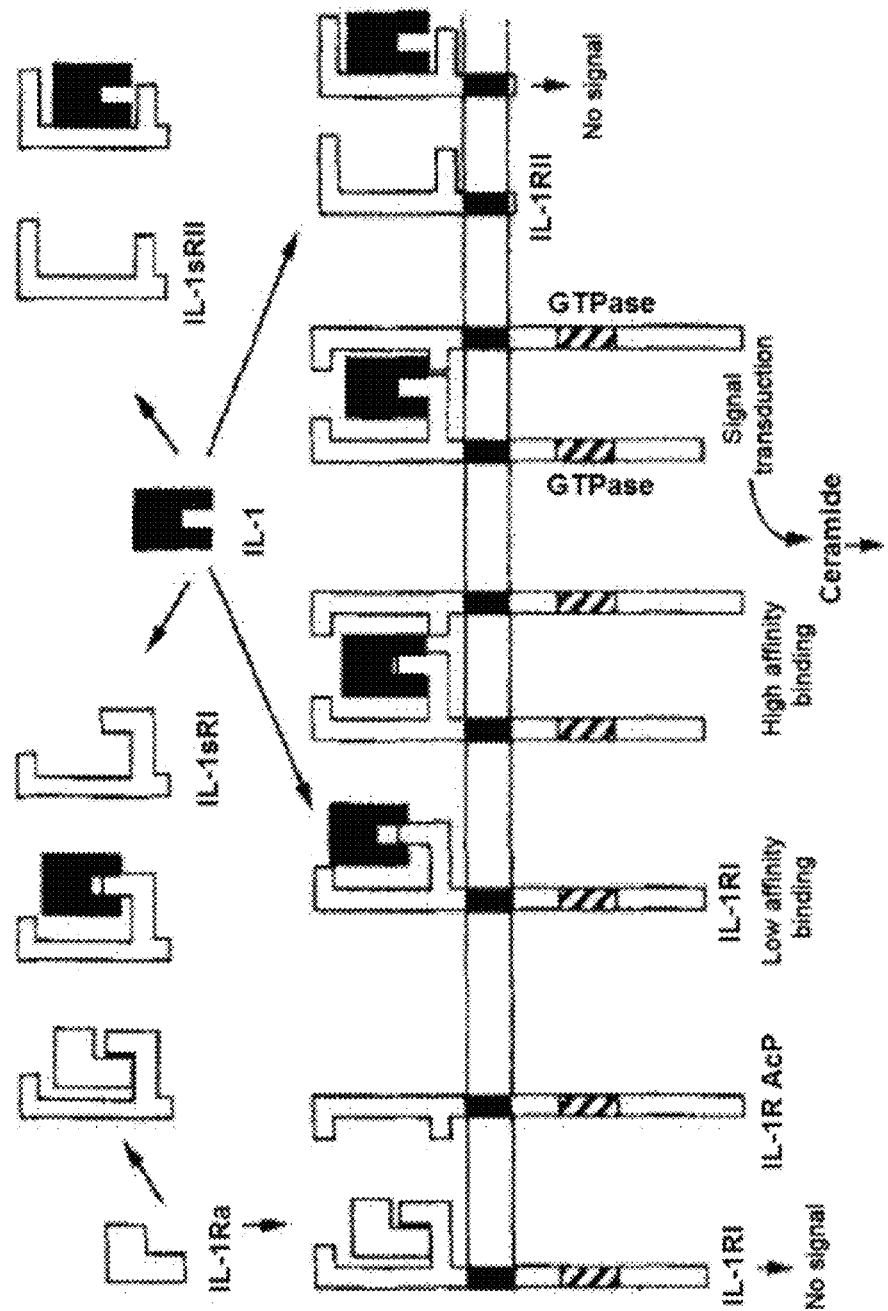
FIG. 20: Signal transduction pathway of interleukin-1 family.

FIG. 20 is the signal transduction pathway diagram of the interleukin-1 family (the published paper: Charles A. Dinarello. Biological Basis for Interleukin-1 in Disease. *Blood, Vol* 87, No 6 (March 15), 1996: pp 2095-2147). In the FIG. 20:

IL-1Ra interleukin-1 receptor antagonist
IL-1sRI interleukin-1 soluble receptor type I
IL-1 interleukin-1
IL-1sRII interleukin-1 soluble receptor type II
IL-1RI interleukin-1 receptor type I
IL-1RAcP interleukin-1 receptor accessory protein
IL-1RII interleukin-1 receptor type II Combined with this figure and the public knowledge of the existing technology, the technicians in this field can easily know the following:

After IL-1 combines with IL-1RI, they can form high-affinity ligand and receptor binding with the help of IL-1RI-AcP, and thus start the signal transduction. This signal transduction is regulated by a variety of factors, and comments are as follows:

Binding of IL-1Ra to IL-1RI, results in no signal transduction (No signal), and decreases in the number of cell surface IL-1RI which interacts with IL-1;

Binding of IL-1 to IL-1sRI reduces free IL-1 resulting in the decreased interaction of IL-1 and IL-1RI.

Binding of IL-1 to IL-1 sRII reduces free IL-1 resulting in the decreased combination of IL-1 and IL-1RI.

Binding of IL-1 to IL-1RII results in no signal transduction (No signal) which reduces free IL-1 and results in the decreased interaction of IL-1 and IL-1RI.

In addition, because the antibody has the characteristics of specific binding of antigen, the antigen-antibody binding will directly block antigen interaction with its natural protein, thus affecting the biological function of antigen protein. According to FIG. 20, the technicians in this field can easily understand the methods of blocking IL-1 signal transduction:

Anti-IL-1 antibody interacting with IL-1 prevents the binding of IL-1 to IL-1RI resulting in the block of IL-1 signaling pathway.

Anti-IL-1RI antibody interacting with IL-1RI prevents the binding of IL-1RI to IL-1 resulting in the block of IL-1 signaling pathway.

Anti-IL-1RAcP antibody interacts with IL-1RAcP to prevent the formation of high affinity binding of IL-1 and IL-1RI. And thereby, it blocks the IL-1 signaling pathway.

Example 1

The protective effect of IL-1Ra pretreatment on small intestine of chemotherapy treated mice. IL-1Ra pretreatment protects small intestine of the mice treated by single injection of cyclophosphamide.

BALB/c mice (SPF grade, 8 weeks old, body weight 23-28 g) were divided into two groups randomly. The first group was injected with recombinant human IL-1Ra (rhIL-1Ra) (amino acid sequence as shown in SEQ ID NO: 1) (1 mg/kg b.w. I.P., injected once every 24 hours) for 3 continuous days from day −3 to day −1; the second group was injected with equal volumes of saline (I.P., injected once every 24 hours). At day 0, i.e. 12 hours after the last injection with protein or saline, cyclophosphamide (CTX) was injected once (300 mg/kg b.w. I.P.). Outcome measures: H&E stained small intestinal sections. The small intestine of location 15 mm below the stomach of each mouse was harvested and sliced; the average length of villus and crypts of each mouse was calculated by averaging 40 villus and crypts equally from 4 sections.

Figure 2:
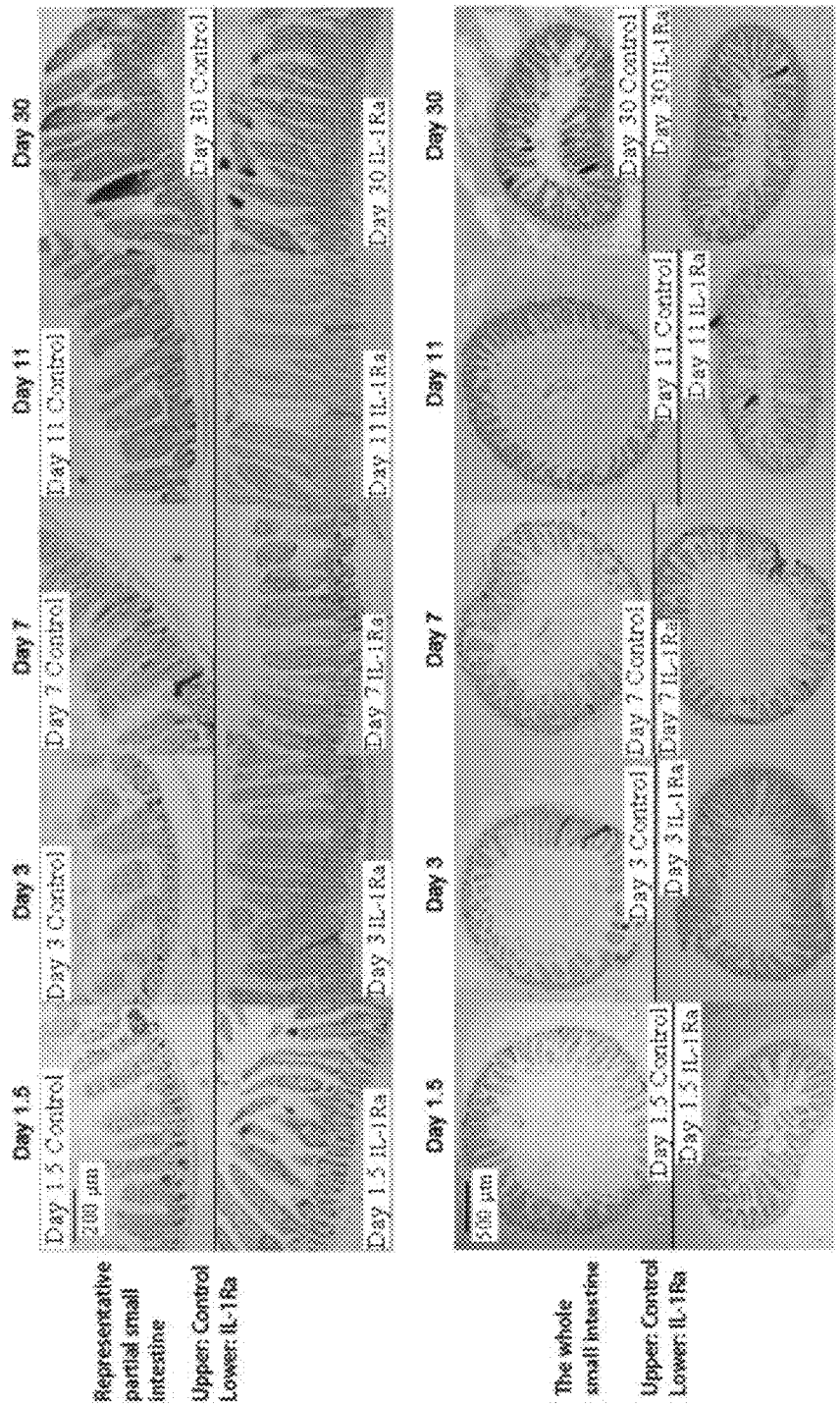
FIG. 2: The H&E stained tissue sections of the intestines from the mice that received preventive treatment of IL-1Ra before single dose cyclophosphamide chemotherapy.

Results: Statistics of H&E stained small intestinal sections. The small intestinal damage post-chemotherapy was characterized by shorter villus and crypts. Administration of rhIL-1Ra before chemotherapy effectively protected villus length and crypts depth. At days 1.5, 3 and 11, the intestinal villus length of rhIL-1Ra treated group was evidently longer than the control group (P<0.05, two-tailed Student's t-test). At day 7, compared with the control group, the intestinal crypts depth of rhIL-1Ra treated group increased significantly (P<0.05, two-tailed Student's t-test) (FIGS. 1, 2 and tables 1, 2).

TABLE 1

| Villus length (μm) | | | | | | |
|---|---|---|---|---|---|---|
| Villus length | Day 0 | Day 1.5 | Day 3 | Day 7 | Day 11 | Day 30 |
| Mean of control group | 448.65 | 344.68 | 273.59 | 282.36 | 244.89 | 375.96 |
| SD of control group | 29.94 | 67.6 | 40.13 | 13.99 | 62.38 | 47.27 |
| Mean of rhIL-1Ra treated group | 371.08 | 454.39 | 343.14 | 307.1 | 362.92 | 331.58 |
| SD of rhIL-1Ra treated group | 102.94 | 46.18 | 39.77 | 15 | 13.41 | 24.41 |
| P value | 0.414 | 0.011 | 0.049 | 0.052 | 0.01 | 0.146 |

TABLE 2

| Crypts depth (μm) | | | | | | |
|---|---|---|---|---|---|---|
| Crypts depth | Day 0 | Day 1.5 | Day 3 | Day 7 | Day 11 | Day 30 |
| Mean of control group | 80.02 | 63.3 | 61.66 | 61.15 | 65.73 | 68.25 |
| SD of control group | 12.13 | 8.26 | 8.73 | 2.46 | 7.96 | 5.93 |
| Mean of rhIL-1Ra treated group | 80.05 | 68.37 | 63.55 | 66.89 | 74.9 | 71.9 |
| SD of rhIL-1Ra treated group | 6.95 | 5.24 | 8.86 | 1.99 | 11.6 | 6.08 |
| P value | 0.91 | 0.228 | 0.77 | 0.01 | 0.249 | 0.423 |

Example 2

The protective effect of IL-1Ra pretreatment on small intestine of chemotherapy treated mice. IL-1Ra pretreatment protects the small intestine of the mice treated by cyclophosphamide injections for 3 consecutive days.

BALB/c mice (SPF grade, 8 weeks old, body weight 23-28 g) were divided into two groups randomly. The first group was injected with rhIL-1Ra (1 mg/kg b.w. I.P., injected once every 24 hours) for 5 consecutive days (day −5 to −1); the second group was injected with equal volumes of saline (I.P., injected once every 24 hours). After 24 hours of the last injection with protein or saline, CTX was injected for 3 consecutive days from day 0 to day 2 (200 mg/kg b.w. I.P., injected once every 24 hours). Outcome measures: body weight, food-intake, water-intake, diarrhea and death.

Figure 3:
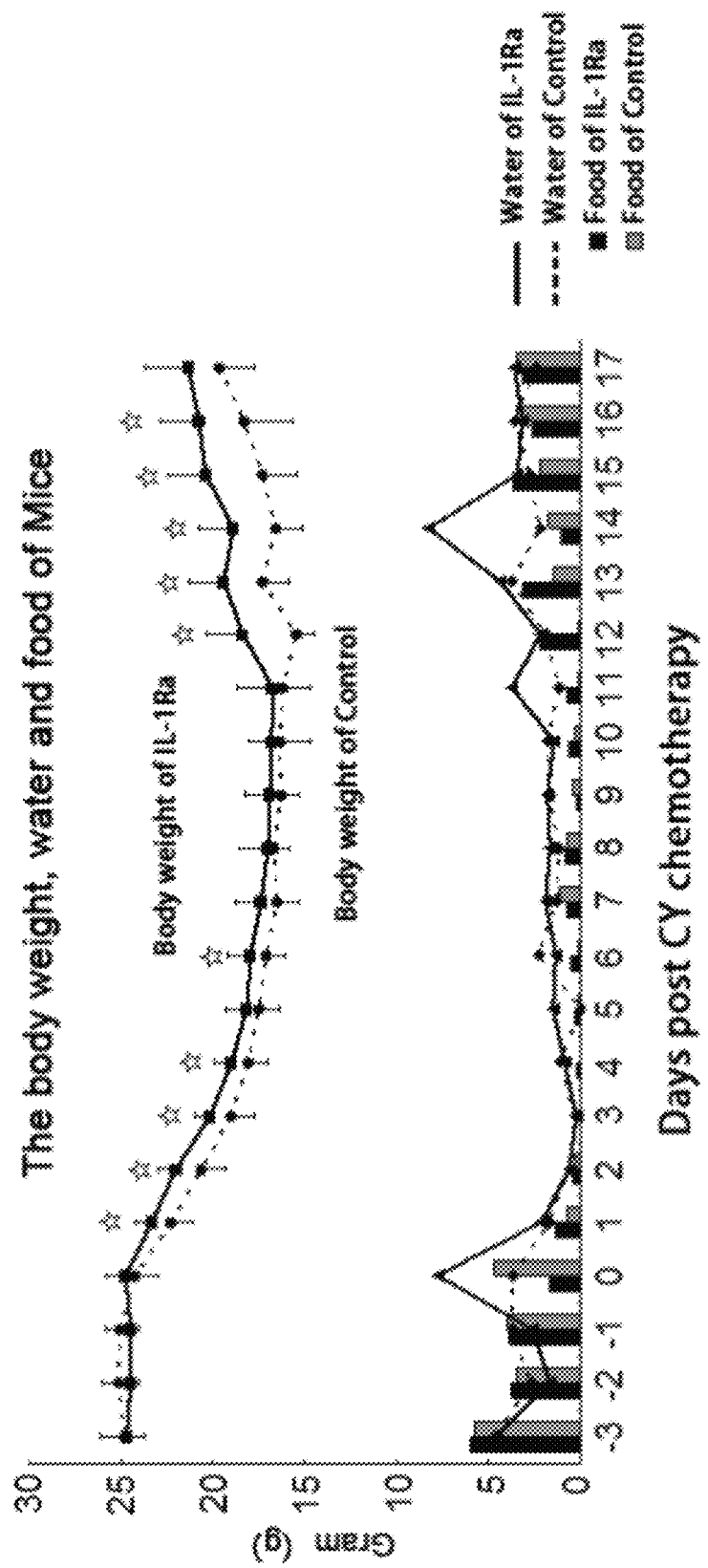
FIG. 3: The effect of IL-1Ra preventive treatment on the body weight of the mice that received cyclophosphamide chemotherapy for 3 consecutive days.

Results: Body weight: in the observation period, the average body weight of rhIL-1Ra treated group was higher than the control group. There were extremely significant differences at days 2, 3, 12, and 15, and significant differences at days 1, 4, 6, 13, and 16 (FIG. 3).

Food-intake: the average food intake of each mouse in rhIL-1Ra treated group was 1.97 g/day, compared with 2.00 g/day in control group. Wherein the average food intake in rhIL-1Ra treated group was higher than the control group at days −3, −2, 1, 2, 3, 4, 5, 6, 8, 10, 11, 12, 13, and 15, and more than 40% at days 1, 3, 4, 5, 6, 10, 11, 12, 13, and 15 (FIG. 3).

Water-intake: the average water intake of each mouse in rhIL-1Ra treated group was 3.08 g/day, compared 2.50 g/day in the control group. And the average water-intake of rhIL-1Ra treated group was higher than the control group at days 0, 1, 5, 7, 8, 9, 11, 12, 13, 14, 15, and 17, and more than 40% at days 0, 5, 7, 8, 11, 14, and 17 (FIG. 3).

Figure 4:
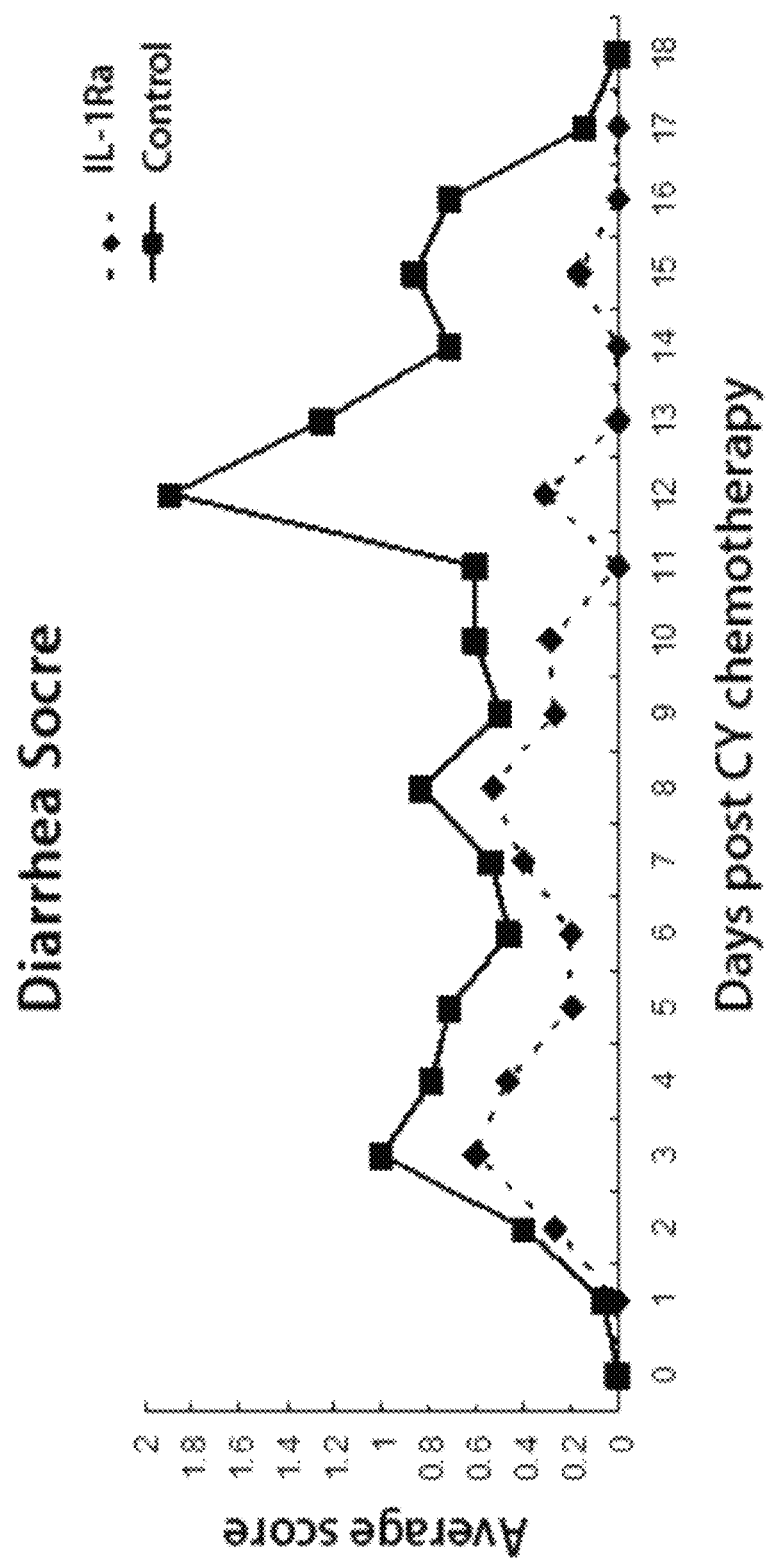
FIG. 4: The effect of IL-1Ra preventive treatment on the diarrhea score of the mice that received cyclophosphamide chemotherapy for 3 consecutive days.

Diarrhea: during the observation period of this experiment, the average diarrhea score of rhIL-1Ra treated group in every day was lower than the control. The average score index of daily diarrhea of each mouse was 0.206 in the treatment group, and 0.614 in the control group (FIG. 4).

Figure 5:
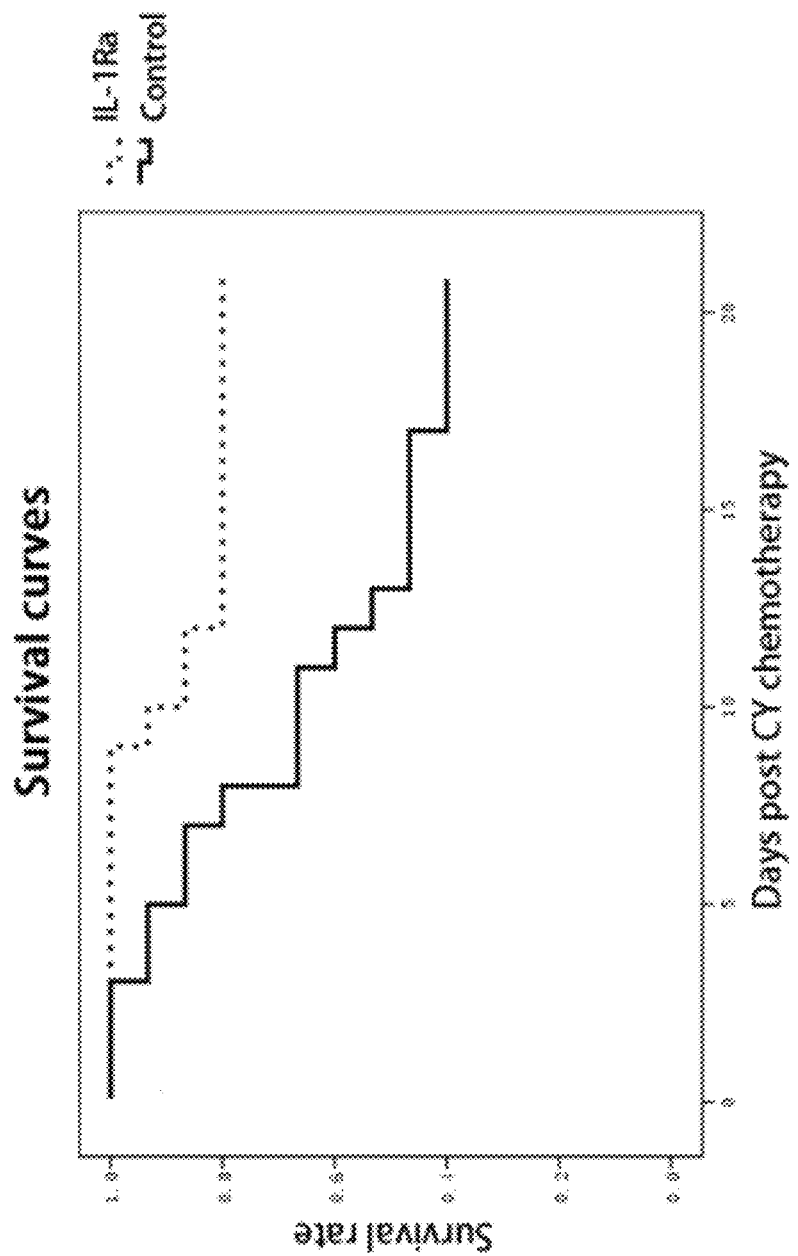
FIG. 5: The effect of IL-1Ra preventive treatment on the survival curves of the mice that received cyclophosphamide chemotherapy for 3 consecutive days.

Survival curves: the average survival time was 18.87 days in rhIL-1Ra treated group, compared with 14 days in the control group, with 35% higher. The survival rate was 80% in rhIL-1Ra treated group, compared with 40% in the control group, with significant differences ($P<0.05$) (FIG. 5).

Example 3

The protective effect of IL-1Ra pretreatment on small intestine of chemotherapy treated mice. IL-1Ra pretreatment protects the small intestine of the mice treated with two cycles of cyclophosphamide chemotherapy.

BALB/c mice (SPF grade, 8 weeks old, body weight 23-30 g) were divided into two groups randomly. The rhIL-1Ra treated group was intraperitoneally injected with 1 mg/kg/day rhIL-1Ra for 3 consecutive days from day −3 to day −1, and the control group was injected with saline (NS) (from day −3 to day −1). At day 0, 200 mg/kg cyclophosphamide (CTX) was intraperitoneally injected into two groups. One month later, rhIL-1Ra and CTX were injected again using the same protocol as the first cycle. The interval of two CTX injections was 30 days. After the second injection of CTX, the body weight of mice and survival rate were observed.

Figure 6:
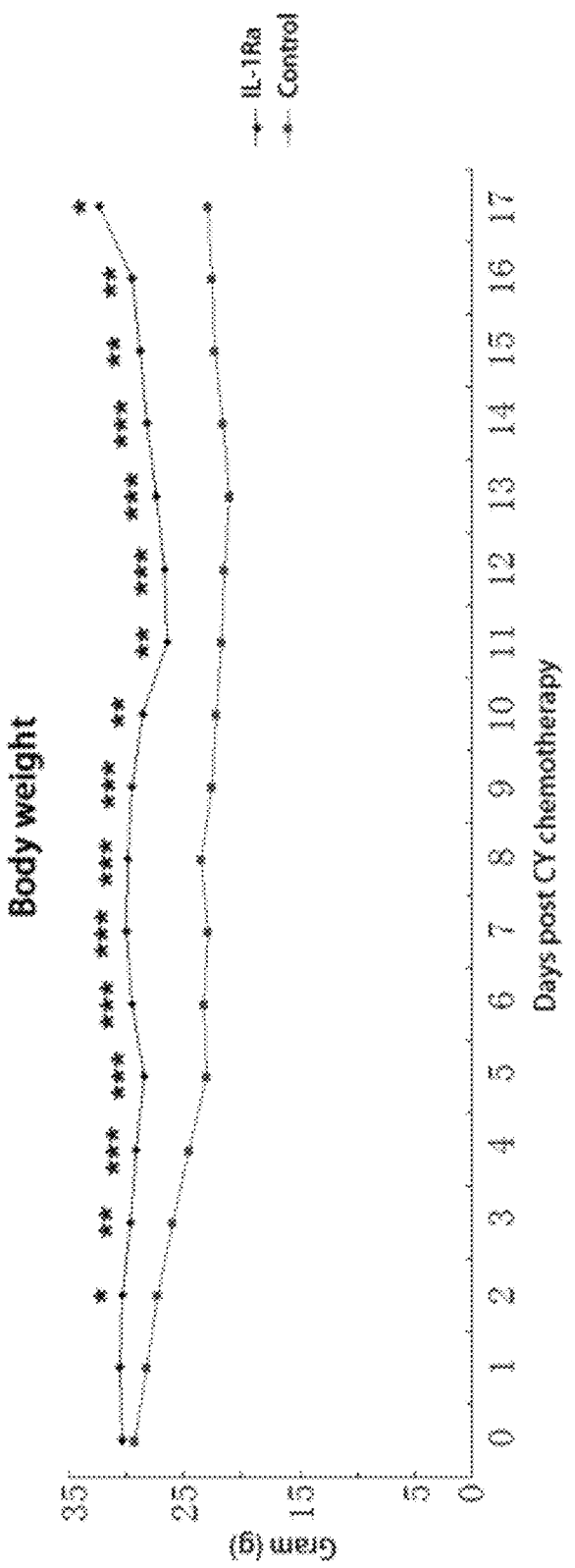
FIG. 6: The effect of IL-1Ra preventive treatment on the body weight of the mice that received two cycles of cyclophosphamide chemotherapy.

Results: The body weight of mice after two cycles of cyclophosphamide chemotherapy (200 mg/kg*2) was obtained. The average body weight of mice in rhIL-1Ra treated group was higher than the control group, wherein from day 4 to day 9 and from day 12 to day 14, there were extremely significant differences between these two groups (two-tailed Student's t-test, $P<0.01$). At days 3, 10, 11, 15, and 16, there were significant differences between these two groups (two-tailed Student's t-test, $P<0.05$), and at Day 2 and 17, there was difference between these two groups (one-tailed Student's t-test, $P<0.05$) (FIG. 6).

Figure 7:
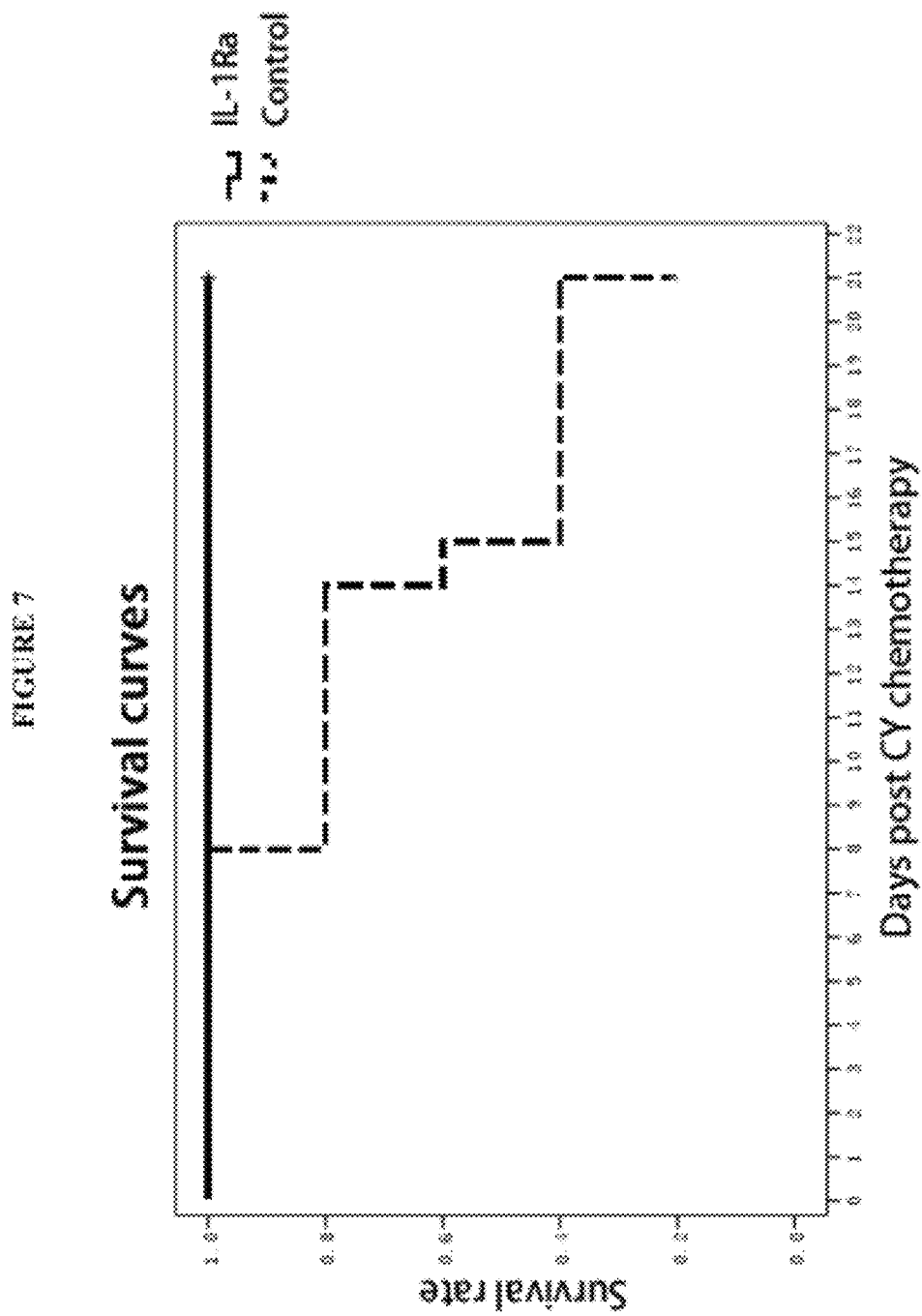
FIG. 7: The effect of IL-1Ra preventive treatment on the survival rate of the mice that received two cycles of cyclophosphamide chemotherapy.

Survival rate: Observed for 21 days, the average survival time of rhIL-1Ra treated group was 21 days and the control group was 15.8 days. Survival rate of rhIL-1Ra treated groups was 100% and the control group was 20%. The difference of survival rate between these two groups was statistically significant ($P<0.05$) (FIG. 7).

Example 4

The protective effect of IL-1Ra pretreatment on small intestine of chemotherapy treated mice. IL-1Ra pretreatment protects the small intestine of the mice treated with two cycles of cyclophosphamide chemotherapy.

BALB/c mice (SPF grade, 8 weeks old, body weight 23-30 g) were divided into two groups randomly. The rhIL-1Ra treated group was intraperitoneally injected with 1 mg/kg/day rhIL-1Ra for 3 consecutive days from day −3 to day −1, and the control group was injected with saline (NS) (from day −3 to day −1). At day 0, 300 mg/kg cyclophosphamide (CTX) was intraperitoneally injected into two groups. One month later, rhIL-1Ra and CTX were injected again using the same protocol as first cycle. The interval of two CTX injections was 30 days. After the second injection of CTX, the body weight of mice were observed (n=8).

Figure 8:
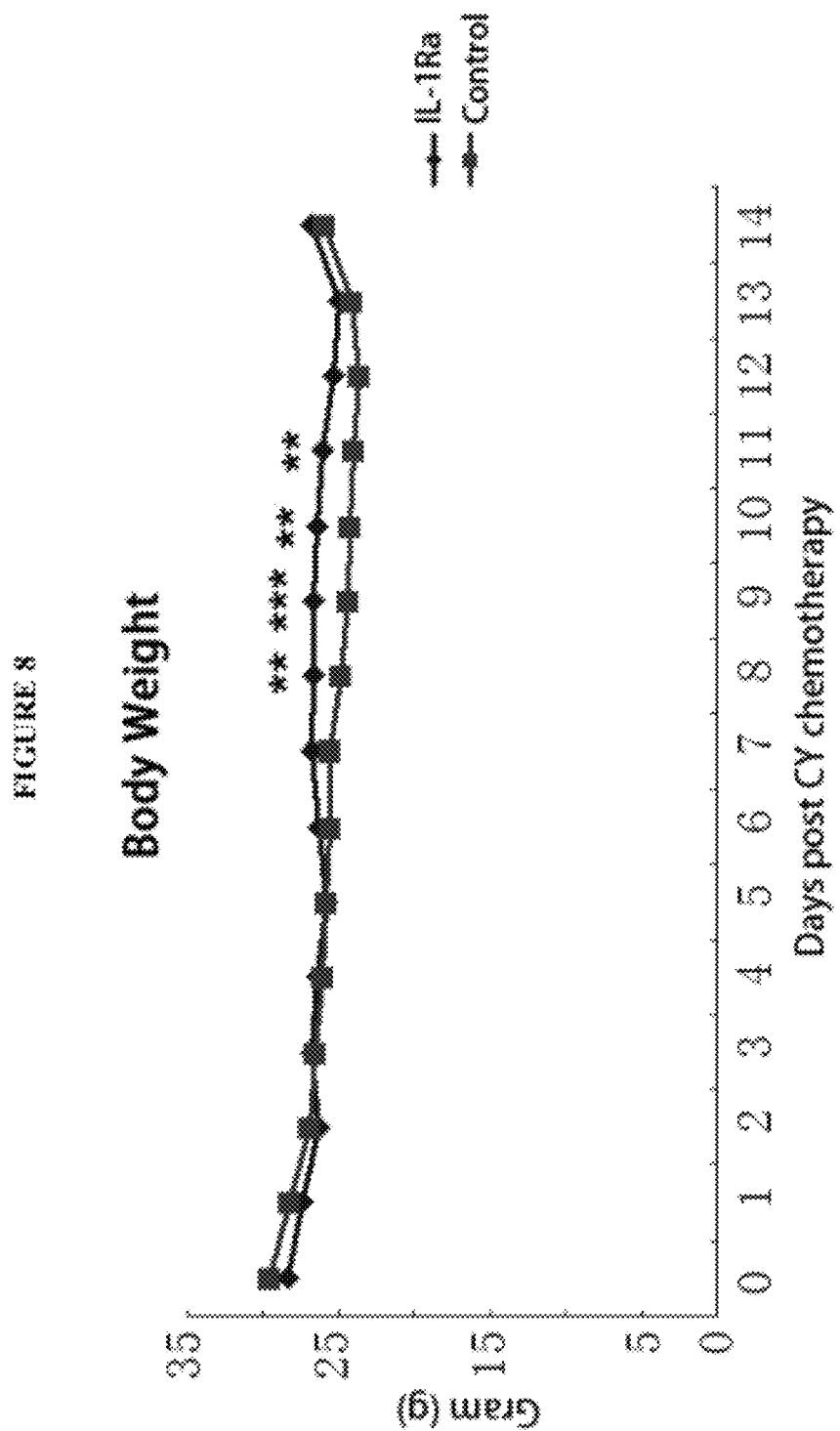
FIG. 8: The effect of IL-1Ra preventive treatment on body weight of the mice that received two cycles of cyclophosphamide chemotherapy.

Results: The body weight of mice after two cycles of cyclophosphamide chemotherapy (300 mg/kg*2) was obtained. The average body weight of mice in rhIL-1Ra treated group was higher than the control group after day 6, wherein at day 9, there were extremely significant differences between these two groups (two-tailed Student's t-test, $P<0.01$). At days 8, 10, 11, there were significant differences between these two groups (two-tailed Student's t-test, $P<0.05$) (FIG. 8).

Example 5

The protective effect of IL-1Ra pretreatment on small intestine of chemotherapy treated mice. IL-1Ra pretreatment protects the small intestine of mice treated with three cycles of cyclophosphamide chemotherapy.

BALB/c female mice (SPF grade, 7-8 weeks old) of rhIL-1Ra treated group were intraperitoneally injected with 1 mg/kg/day rhIL-1Ra for 3 consecutive days from day −3 to day −1, and the control group was injected with saline (NS) (from day −3 to day −1). At day 0, 300 mg/kg cyclophosphamide (CTX) was intraperitoneally injected into all mice. One month later, rhIL-1Ra and CTX were injected again using the same protocol as the first cycle. The interval of two CTX injections was 30 days. One month later, rhIL-1Ra and CTX were injected for the third time using the same protocol as the first two cycles. The interval of two CTX injections was 30 days also. After the third injection of CTX, body weight of mice and survival rate were observed.

Figure 9:
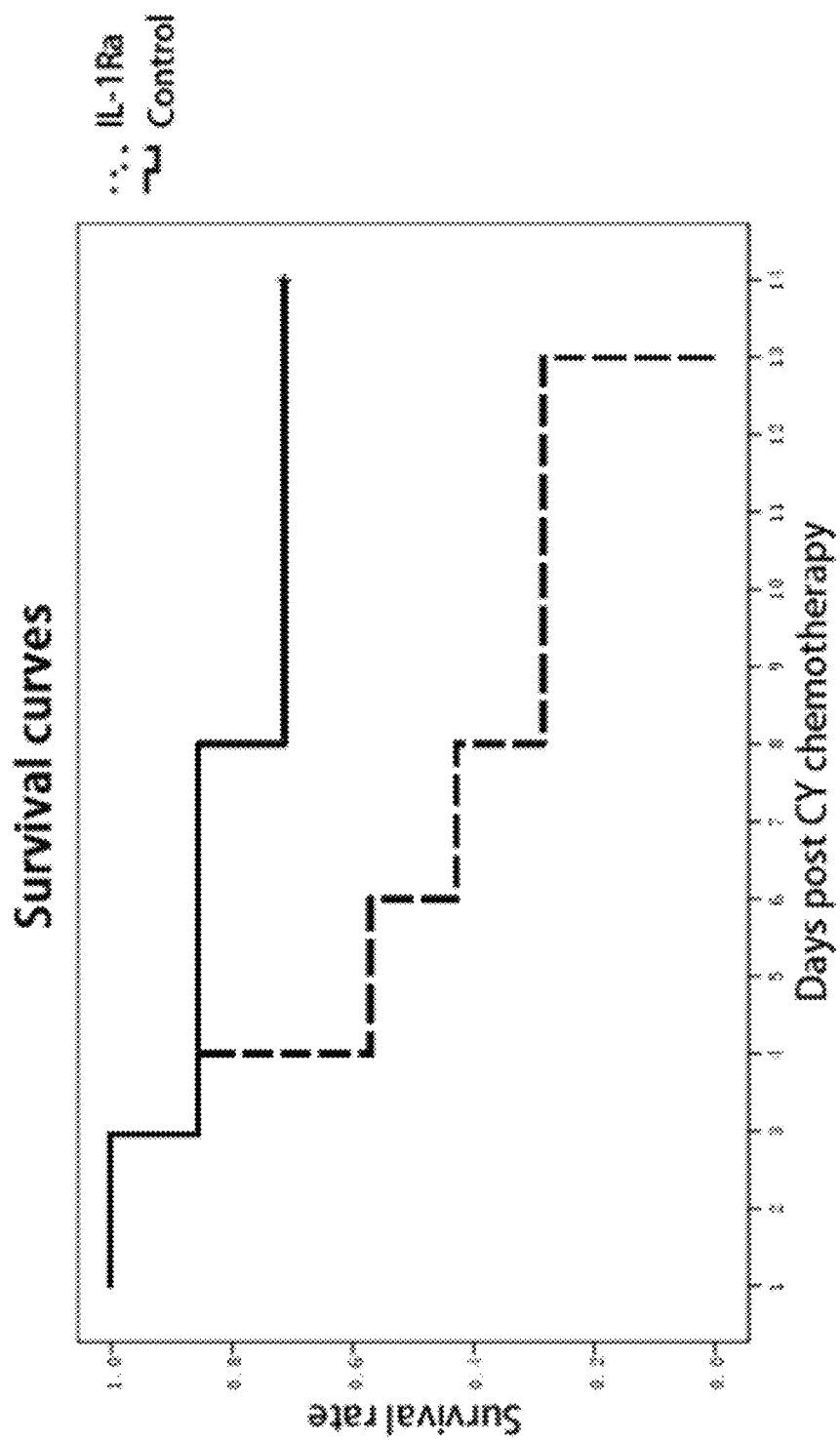
FIG. 9: The effect of IL-1Ra preventive treatment on survival rate of the mice that received three cycles of cyclophosphamide chemotherapy.

Results: The survival rates: Observed for 14 days, the average survival time of rhIL-1Ra treated group was 11.57 days and the control group was 7.29 days. Survival rate of rhIL-1Ra treated group was 71.4% and the control group was 28.6%. The difference of survival rate between these two groups was statistically significant: $P<0.05$ (FIG. 9).

Example 6

The protective effect of IL-1Ra therapeutic treatment on small intestine of chemotherapy treated mice. The therapeutic effect of IL-1Ra injected after 5-fluorouracil chemotherapy.

8-week old BALB/c female mice were intraperitoneally injected with 5-fluorouracil (5-FU) (200 mg/kg) at day 0. After 2 hours, rhIL-1Ra (1 mg/kg) was injected subcutaneously, once a day and a total of 5 times. The control group was injected with the same amount of PBS (phosphate buffered saline). The mice were sacrificed at days 1, 3, 5 and 7 respectively. Their body weight was measured. The small intestine was washed, and 2 cm of the small intestine near the 40% stomach-side was collected and fixed in 4% formaldehyde solution. The tissue sections were prepared. H&E staining was used to measure the injury, and PCNA (cell proliferation core antigen) staining was used to test the cell proliferation.

Figure 10:
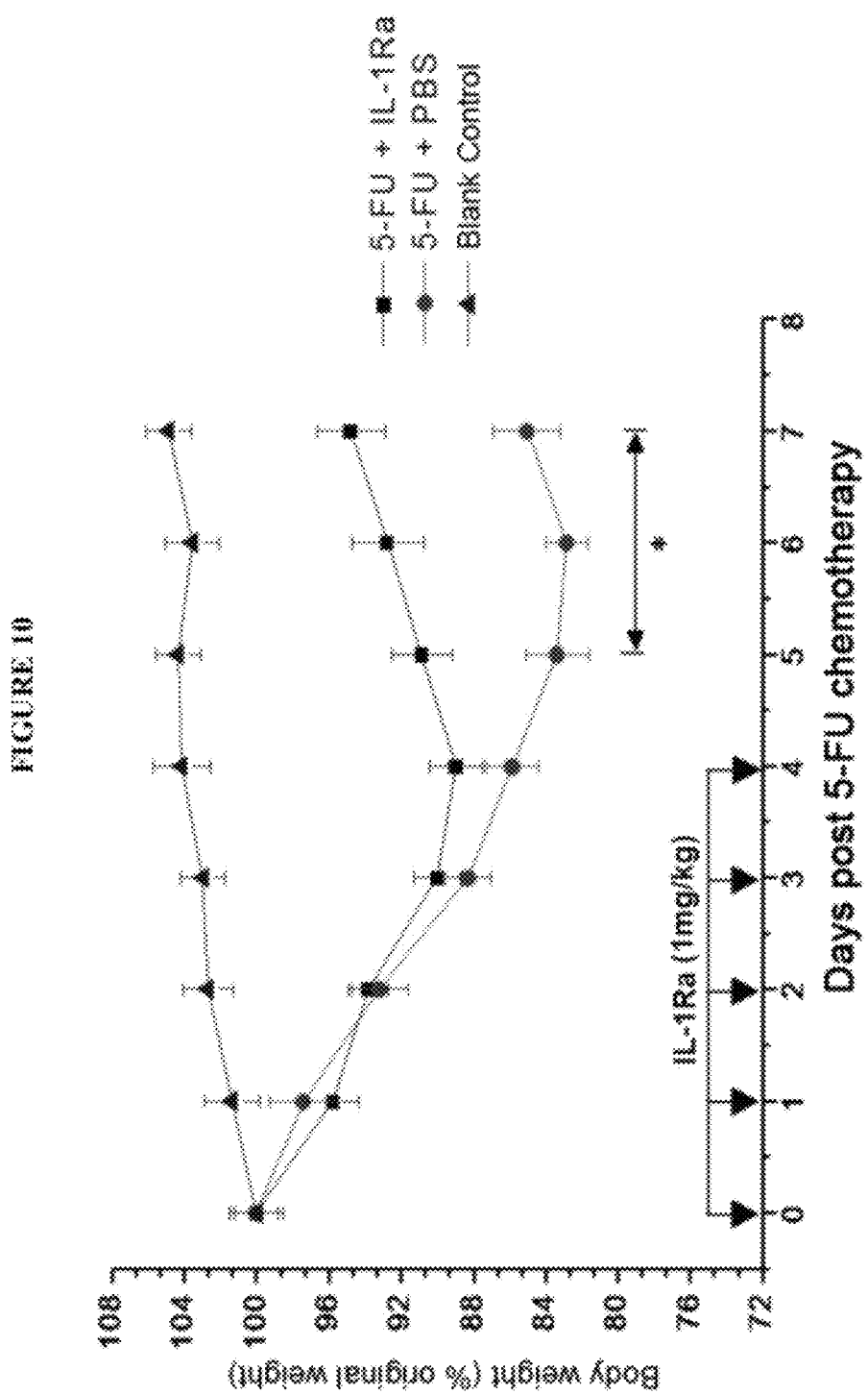
FIG. 10: The effect of IL-1Ra therapeutic treatment on body weight of the mice that received single dose 5-FU chemotherapy.
Figure 11A:
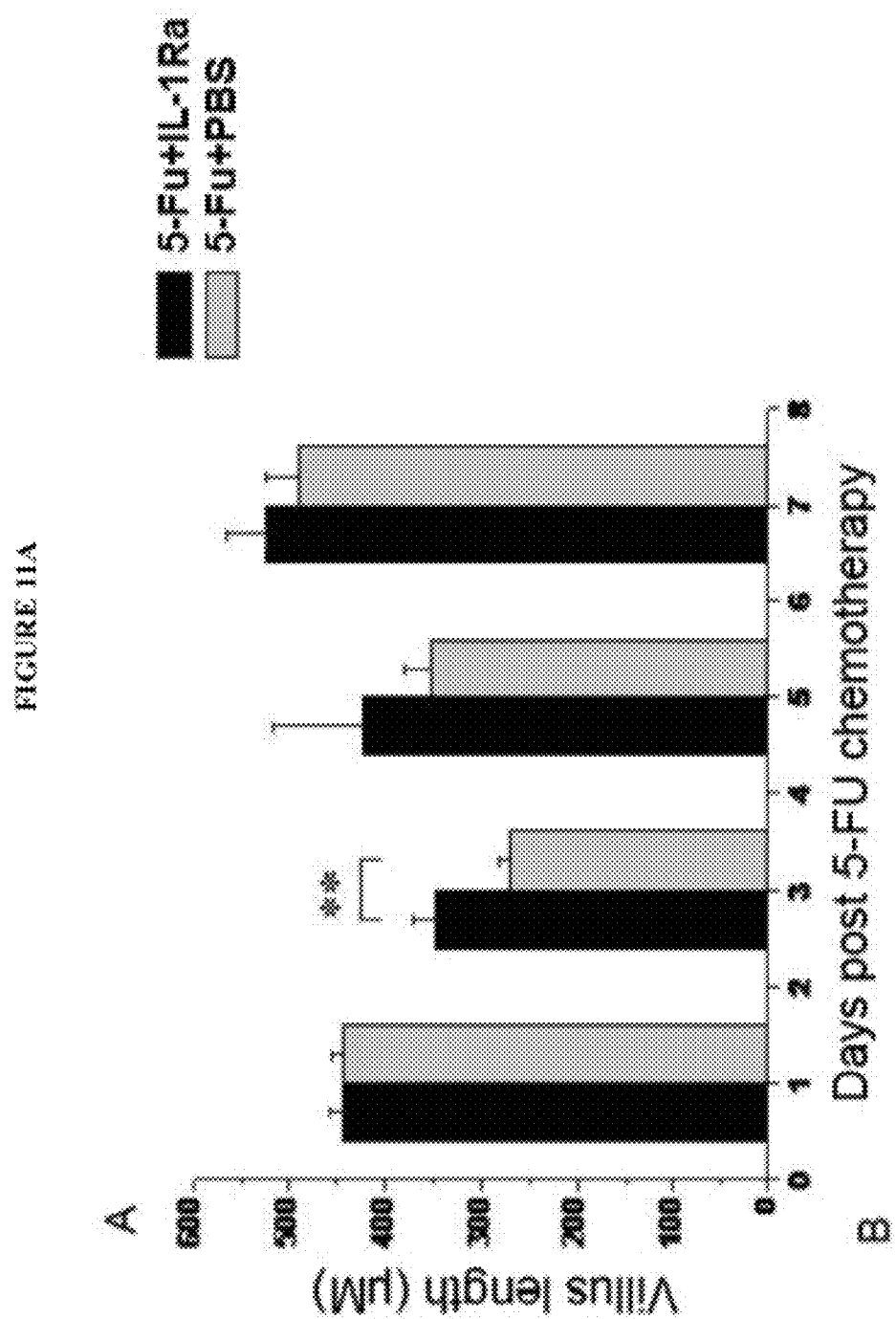
FIG. 11: The effect of IL-1Ra therapeutic treatment on intestinal villus length and crypt depth of the mice received single dose 5-FU chemotherapy.
Figure 11B:
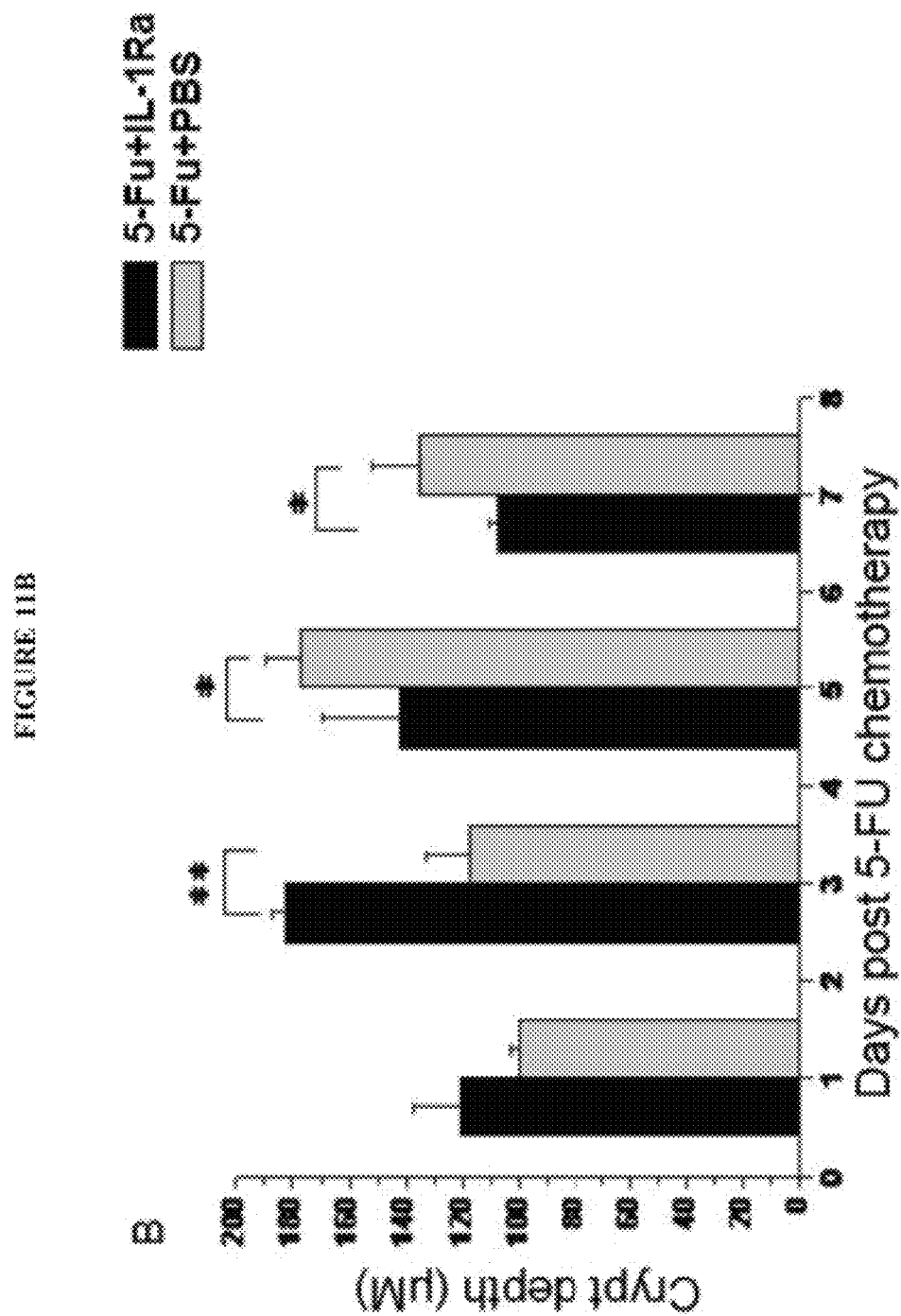
Figure 12:
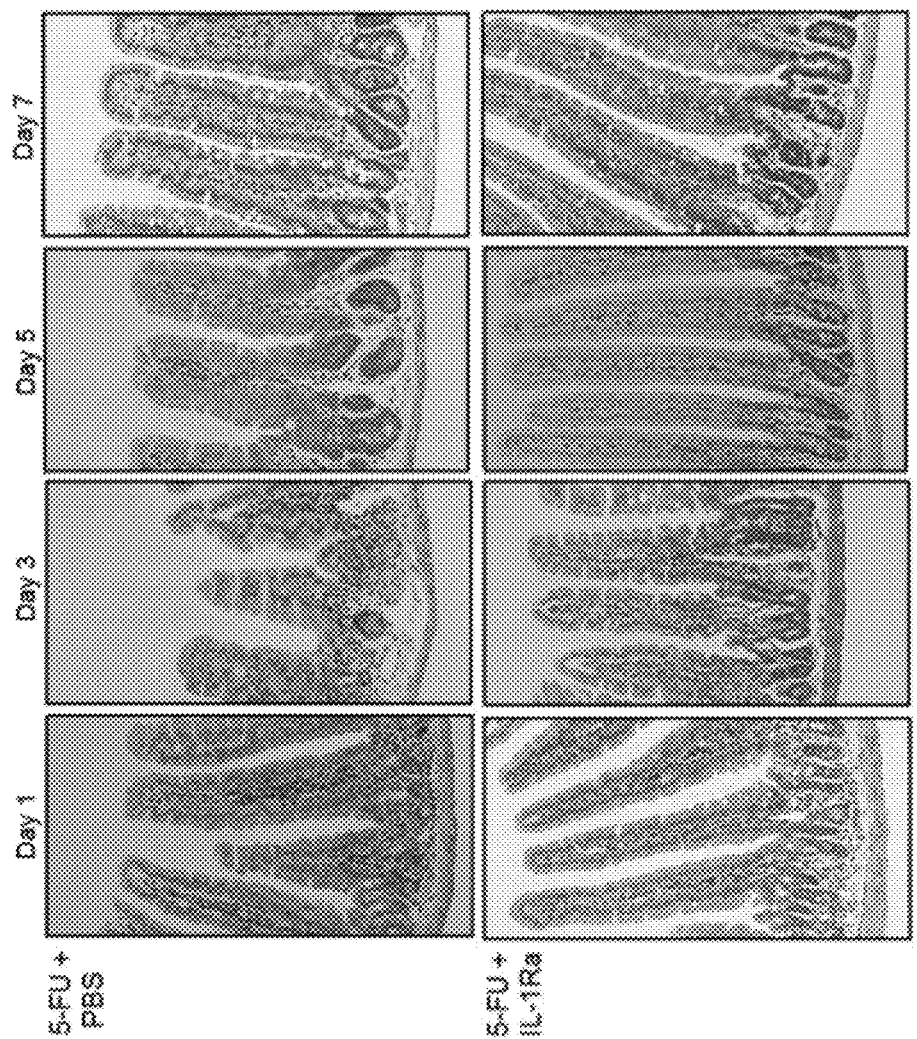
FIG. 12: The H&E stained tissue sections of the intestines from the mice that received therapeutic treatment of IL-1Ra after single dose 5-FU chemotherapy.
Figure 13:
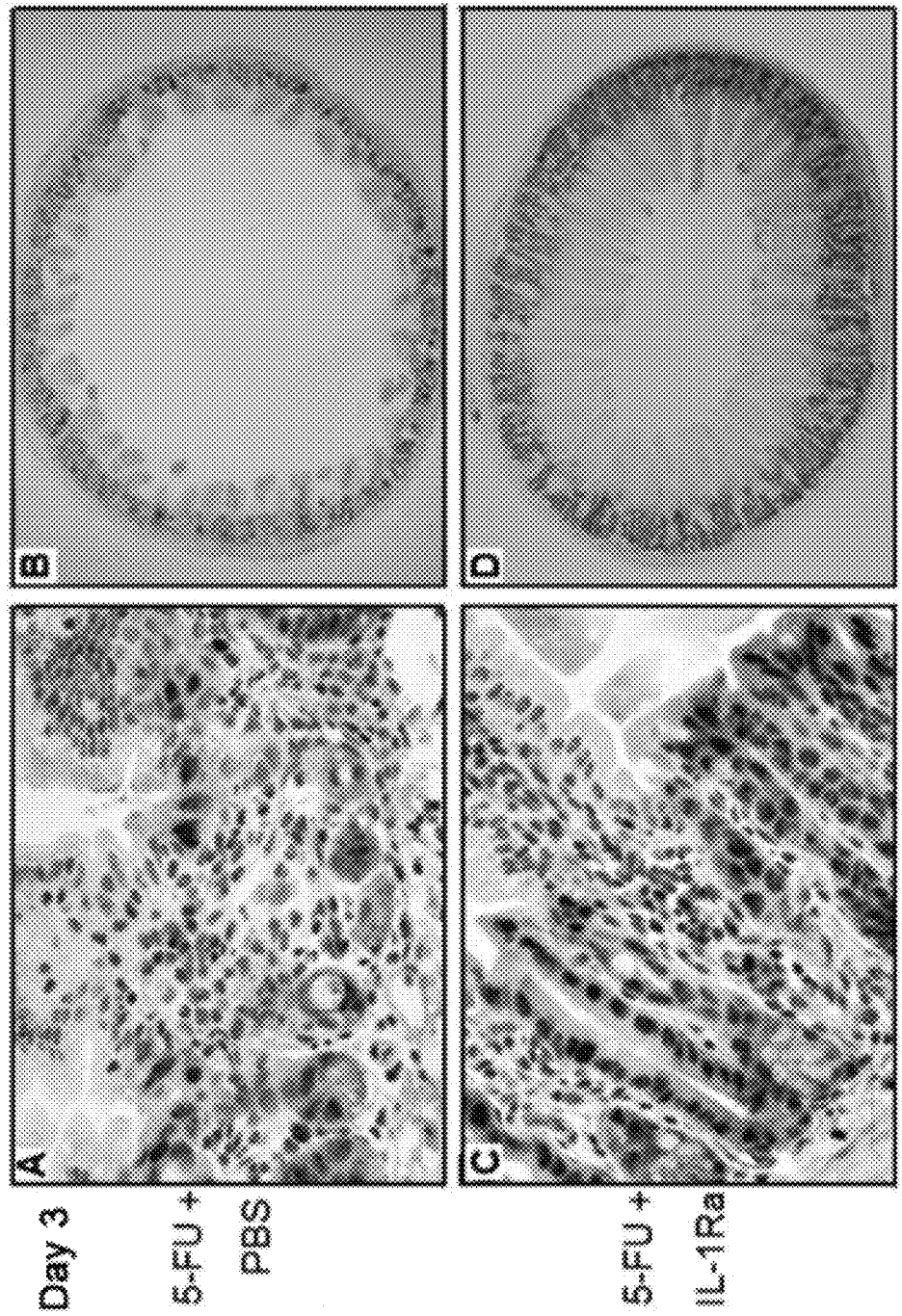
FIG. 13: The PCNA immunohistochemical stained tissue sections of the intestines from the mice that received therapeutic treatment of IL-1Ra after single dose 5-FU chemotherapy.

Results: The body weight showed significant differences between rhIL-1Ra treated group and the control group. In the first three days after chemotherapy, the body weight had no significant differences between these two groups. However, from day 4, the body weight of rhIL-1Ra treated group recovered quickly than the control group, and at day 7, the body weight of rhIL-1Ra treated group recovered almost to the same level before the chemotherapy (FIG. 10). Villus length of rhIL-1Ra treated group was significant longer than the control group at day 3, 5, and 7 (FIGS. 11A, B). More than that, the small intestine of the control group was injured more severely and observed more neutrophil infiltration into small intestine basement than rhIL-1Ra treated group (FIG. 12). We performed proliferative cell nuclear antigen (PCNA) immunohistochemical staining of the tissue sections of day 3 after chemotherapy, which suggested that the number of positive cells in the rhIL-1Ra treated group was evidently more than that of the control group, and the intestinal crypts of the rhIL-1Ra treated group showed more proliferative cells and were comparatively intact than the control group (FIG. 13). Furthermore, according to the references, we used intestinal wet weight/body weight ratio, instead of wet weight, as one of the criterions in evaluating the intestinal pathological changes. As shown in table 3, the ratio of the rhIL-1Ra treated group was larger than the control group in all observed days and showed statistical significance at day 3 (P<0.01), indicating that the small intestine of the rhIL-1Ra treated group was better protected. Meanwhile, the severity of diarrhea was decreased in the rhIL-1Ra treated group (Table 4).

mice. Pretreatment plus therapeutic treatment with IL-1Ra protect small intestine of the mice received single dose cyclophosphamide.

BALB/c mice (SPF grade, 7-8 weeks old) of rhIL-1Ra treated group were intraperitoneally injected with 1 mg/kg/day rhIL-1Ra for 8 consecutive days from day −5 to day 2, and the control group was injected with PBS (from day −5 to day 2). At day 0, 400 mg/kg cyclophosphamide (CTX) was administrated via tail vein injection. The survival time, diarrhea and small intestinal sections of H&E staining were observed. The small intestine of location 15-20 mm below the stomach was sampled from each mouse, and the average length of villus and crypts of each mouse was calculated by averaging 20 villus and crypts equally from 4 sections.

Figure 14:
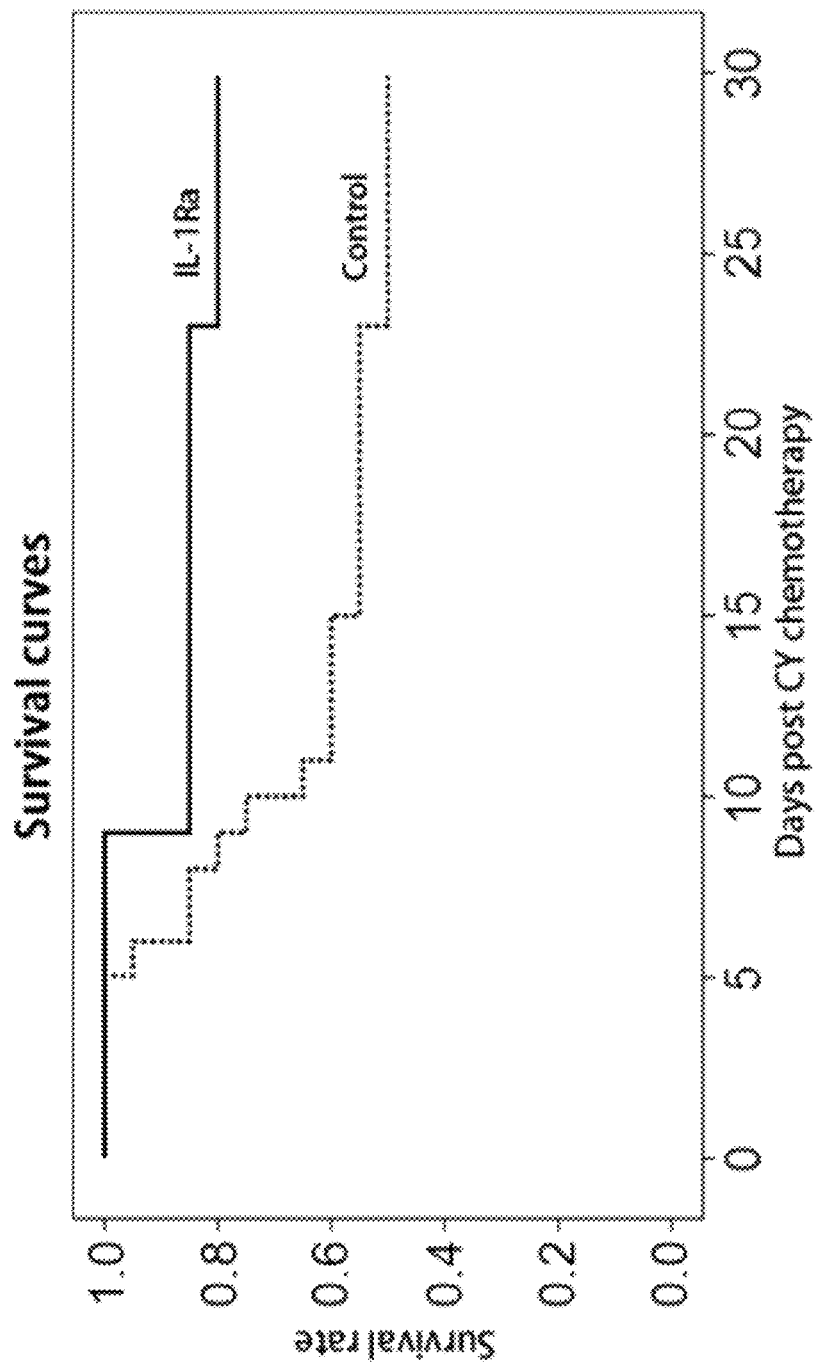
FIG. 14: The effect of IL-1Ra preventive plus therapeutic treatment on survival rate of the mice that received single dose cyclophosphamide chemotherapy.

Results: The mortality (20 mice per group) after single dose cyclophosphamide (400 mg/kg) chemotherapy. The average survival time was 24.9 days in the rhIL-1Ra treated group, compared with 19.15 days in the control group. And the survival rate was increased from 50% of the control group to 80%, with significant differences (Log-Rank, P<0.05) (FIG. 14).

Figure 15:
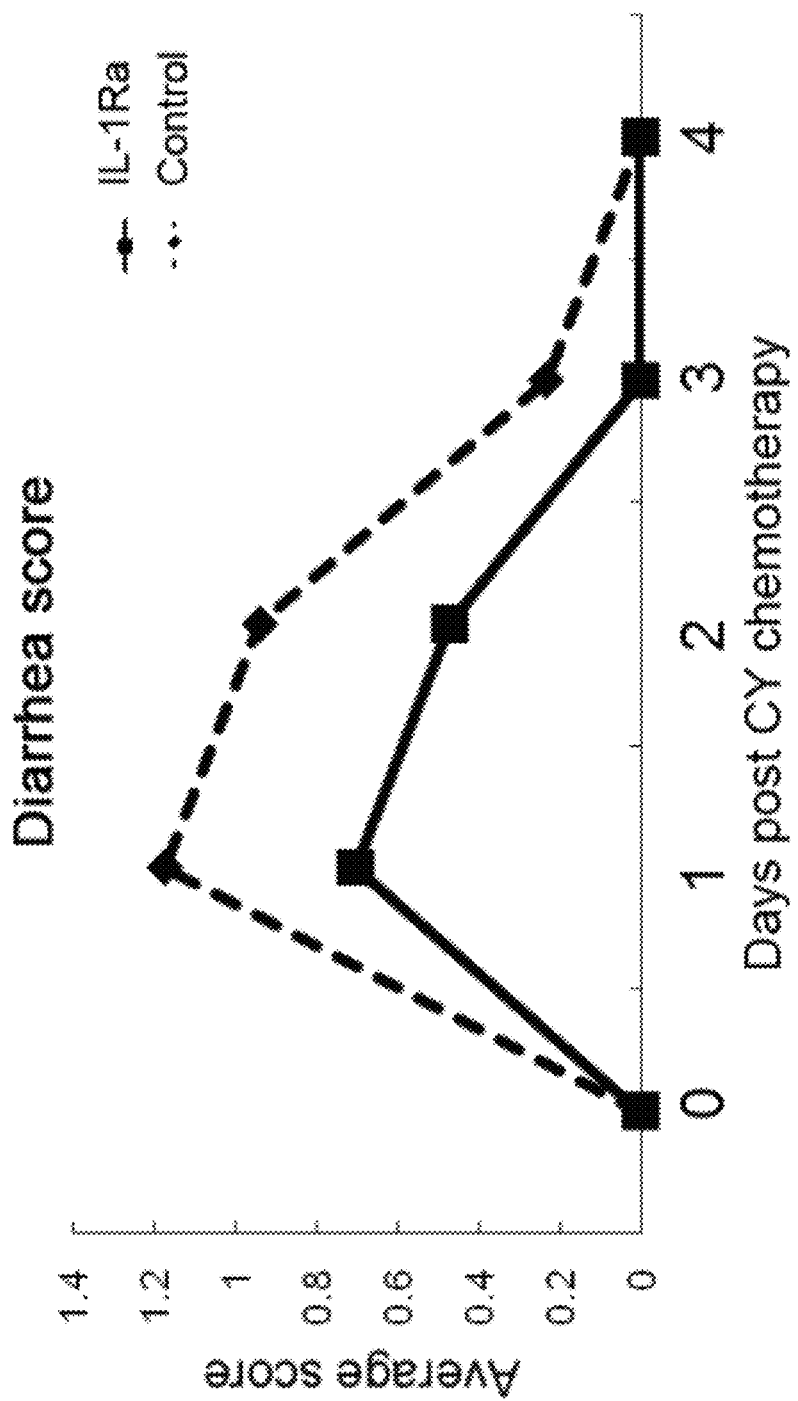
FIG. 15: The effect of IL-1Ra preventive plus therapeutic treatment on diarrhea score of the mice that received single dose cyclophosphamide chemotherapy.

The severity of diarrhea after single dose cyclophosphamide (400 mg/kg) chemotherapy. The severity of diarrhea in the rhIL-1Ra treated group was significantly lower than the control group (FIG. 15).

Figure 16:
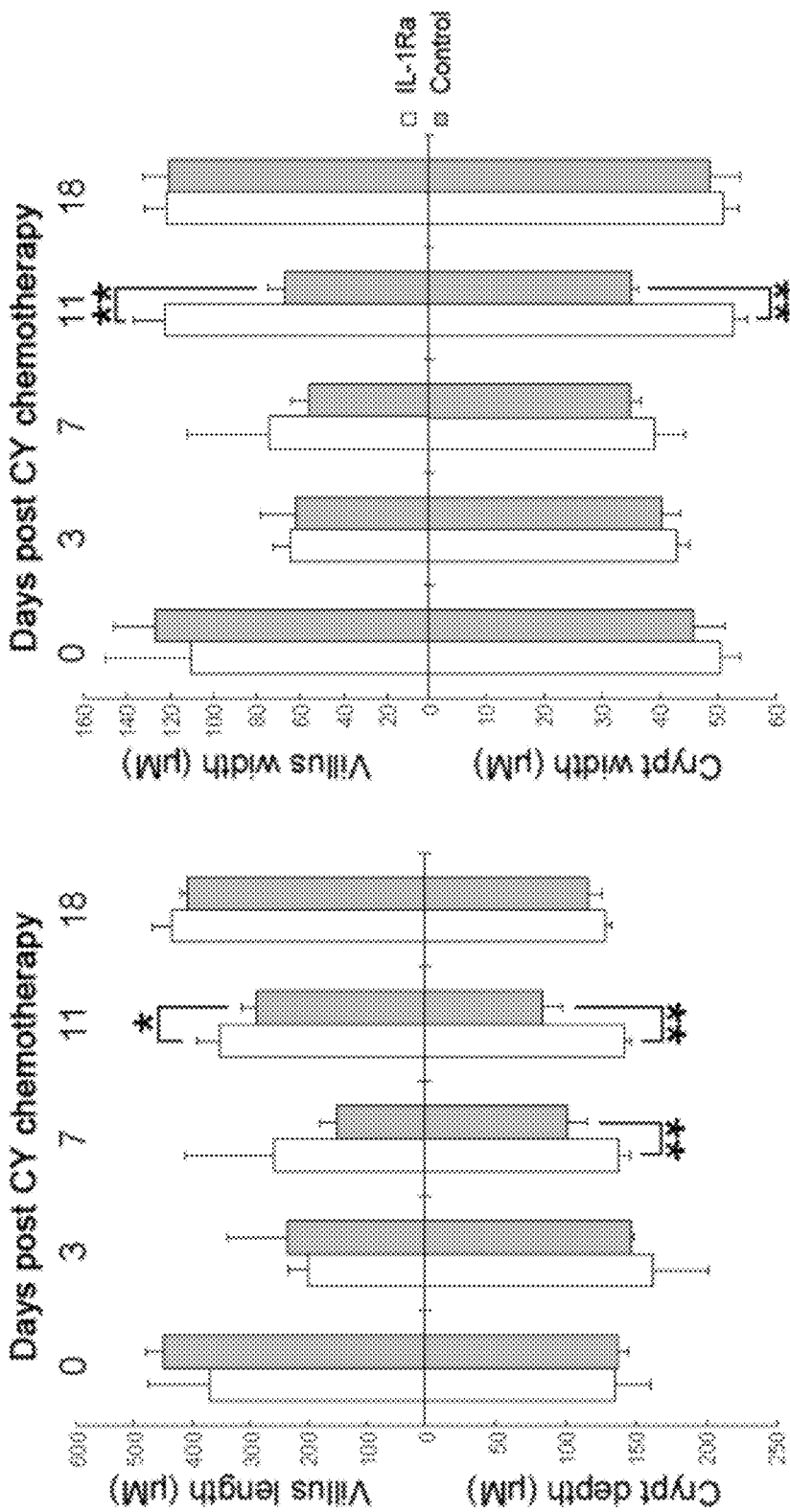
FIG. 16: The effect of IL-1Ra preventive plus therapeutic treatment on intestinal villus length and crypt depth of the mice that received single dose cyclophosphamide chemotherapy.
Figure 17:
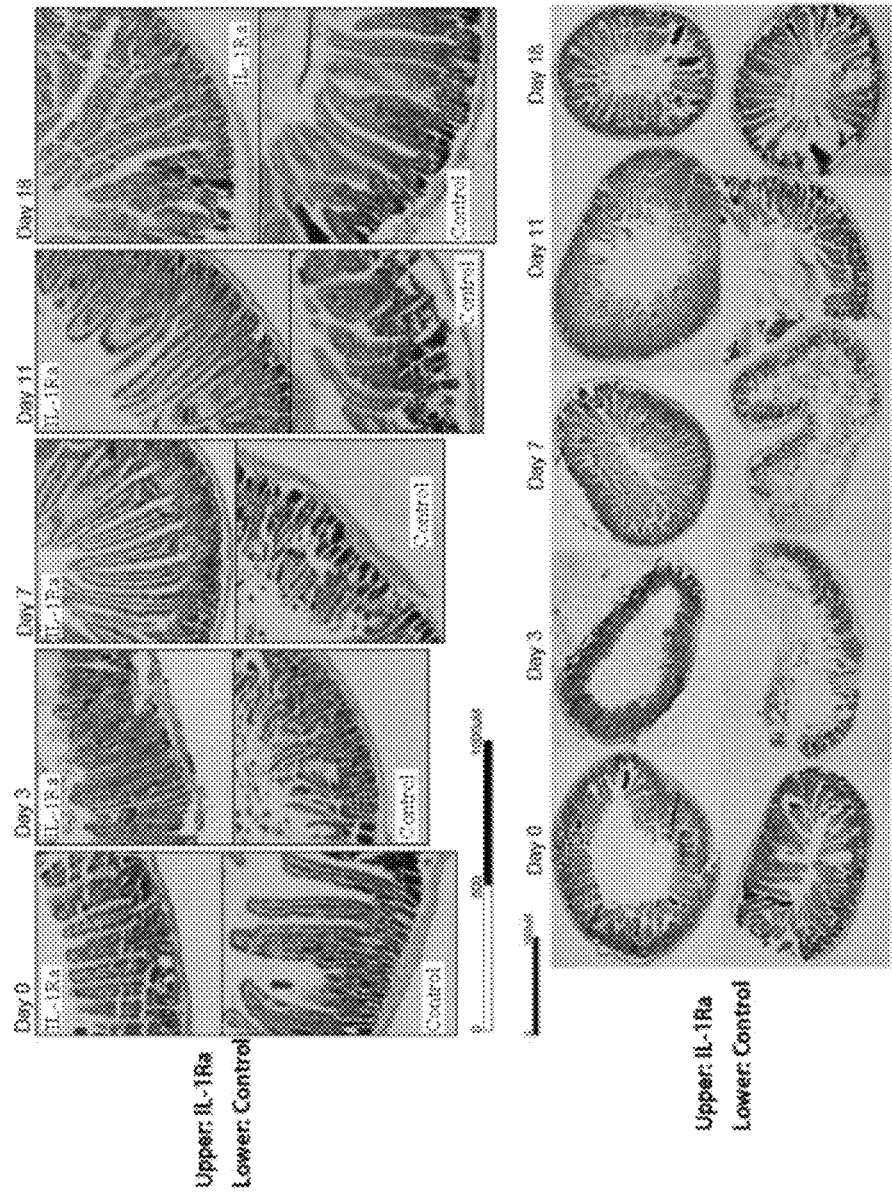
FIG. 17: The H&E stained tissue sections of the intestines from the mice that received preventive plus therapeutic treatment of IL-1Ra before and after single dose cyclophosphamide chemotherapy.

Statistics of H&E stained small intestinal sections. The small intestinal damage post-chemotherapy was characterized by shorter villus and crypts. Administration of rhIL-1Ra effectively protected villus length and crypts depth. At days 1.5, 3 and 11, the intestinal villus length of the rhIL-1Ra treated group was evidently longer than the control group (P<0.05, two-tailed Student's t-test). At day 7, compared with the control group, the villus length of the rhIL-1Ra treated group increased significantly (P<0.05, one-tailed Student's t-test). At day 7, compared with the control group, the intestinal crypts depth of the rhIL-1Ra treated group increased significantly (P<0.05, two-tailed Student's t-test) (Tables 5, 6, 7, 8 and FIGS. 16, 17).

The small intestinal wall of the control group was seriously damaged after chemotherapy, in which crypts were totally destroyed, but it was not happened in the rhIL-1Ra treated group (Table 9).

TABLE 3

Wet weight of small intestine (g/1000 g body weight)

|       | Control      | 5-FU + PBS     | 5-FU + rhIL-1Ra |
|-------|--------------|----------------|-----------------|
| Day 1 |              | 42.89 ± 2.12 ◆ | 47.82 ± 2.43 *  |
| Day 3 |              | 35.07 ± 1.37 ◆◆| 42.23 ± 1.46 ** |
| Day 5 |              | 50.47 ± 2.39 ◆ | 58.32 ± 2.18 *  |
| Day 7 | 54.35 ± 2.17 | 58.05 ± 2.45   | 61.64 ± 2.12    |

TABLE 4

|      |         | Diarrhea score | |
|------|---------|-------|-------|
| 5-FU | rhIL-1Ra | Day 3 | Day 5 |
| −    | −       | −     | −     |
| −    | +       | −     | −     |
| +    | −       | 2.5   | 1.6   |
| +    | +       | 0.8   | 0.3   |

Example 7

The protective effect of IL-1Ra pretreatment plus therapeutic treatment on small intestine of chemotherapy treated

TABLE 5

Villus length (μm)

| Villus length | Day 0 | Day 3 | Day 7 | Day 11 | Day 18 |
|---|---|---|---|---|---|
| Mean of rhIL-1Ra treated group | 371.077 | 201.757 | 256.845 | 352.705 | 434.256 |
| SD of rhIL-1Ra treated group | 102.943 | 32.636 | 156.324 | 38.53 | 32.491 |
| Mean of control group | 448.65 | 237.174 | 151.795 | 289.642 | 408.852 |
| SD of control group | 29.943 | 99.527 | 27.053 | 25.357 | 9.429 |
| P value | 0.414 | 0.524 | 0.232 | 0.034 | 0.184 |

TABLE 6

Villus width (μm)

| Villus width | Day 0 | Day 3 | Day 7 | Day 11 | Day 18 |
|---|---|---|---|---|---|
| Mean of rhIL-1Ra treated group | 110.103 | 65.190 | 74.793 | 121.962 | 121.204 |
| SD of rhIL-1Ra treated group | 39.797 | 7.663 | 37.098 | 15.334 | 10.632 |
| Mean of control group | 127.009 | 61.980 | 55.694 | 67.357 | 120.562 |
| SD of control group | 18.915 | 16.012 | 8.637 | 7.688 | 11.580 |
| P value | 0.642 | 0.730 | 0.352 | 0.001 | 0.938 |

TABLE 7

Crypt depth (μm)

| Crypt depth | Day 0 | Day 3 | Day 7 | Day 11 | Day 18 |
|---|---|---|---|---|---|
| Mean of rhIL-1Ra treated group | 134.945 | 161.13 | 137.855 | 141.377 | 127.591 |
| SD of rhIL-1Ra treated group | 24.888 | 40.114 | 7.137 | 4.854 | 4.249 |
| Mean of control group | 137.27 | 145.952 | 101.056 | 83.178 | 115.422 |
| SD of control group | 6.948 | 1.718 | 13.459 | 13.931 | 10.133 |
| P value | 0.91 | 0.478 | 0.008 | 0.000 | 0.068 |

TABLE 8

Crypt width (μm)

| Crypt width | Day 0 | Day 3 | Day 7 | Day 11 | Day 18 |
|---|---|---|---|---|---|
| Mean of rhIL-1Ra treated group | 50.344 | 42.693 | 38.877 | 52.475 | 50.772 |
| SD of rhIL-1Ra treated group | 3.405 | 2.263 | 5.45 | 2.58 | 2.648 |
| Mean of control group | 45.582 | 40.259 | 34.641 | 34.909 | 48.444 |
| SD of control group | 5.599 | 3.099 | 2.059 | 1.374 | 5.353 |
| P value | 0.412 | 0.252 | 0.204 | 0.000 | 0.465 |

TABLE 9

The area ratio of completely destroyed intestinal wall to total intestinal wall

| | | | |
|---|---|---|---|
| Control group | 1$^{st}$ mouse at day 3 | 28.17% | The mean of day 3 of control group |
| Control group | 2$^{nd}$ mouse at day 3 | 0.00% | 11.66% |
| Control group | 3$^{rd}$ mouse at day 3 | 18.47% | |
| Control group | 4$^{th}$ mouse at day 3 | 0.00% | |
| Control group | 1$^{st}$ mouse at day 7 | 42.24% | The mean of day 7 of control group |
| Control group | 2$^{nd}$ mouse at day 7 | 0.00% | 24.98% |
| Control group | 3$^{rd}$ mouse at day 7 | 41.84% | |
| Control group | 4$^{th}$ mouse at day 7 | 15.83% | |

The completely destroyed intestine was not observed at day 3 and day 7 in the rhIL-1Ra treated group.

Example 8

The protective effect of IL-1Ra pretreatment plus therapeutic treatment on small intestine of chemotherapy treated mice. Pretreatment plus therapeutic treatment with IL-1Ra protect small intestine of mice received single dose cyclophosphamide.

BALB/c mice (SPF grade, 7-8 weeks old) of the rhIL-1Ra treated group were intraperitoneally injected with 1 mg/kg/day rhIL-1Ra for 8 continuous days from day −5 to day 2, and the control group was injected with PBS (from day −5 to day 2). At day 0, 550 mg/kg cyclophosphamide (CTX) was intravenously injected into all mice. The survival and diarrhea were observed.

Figure 18:
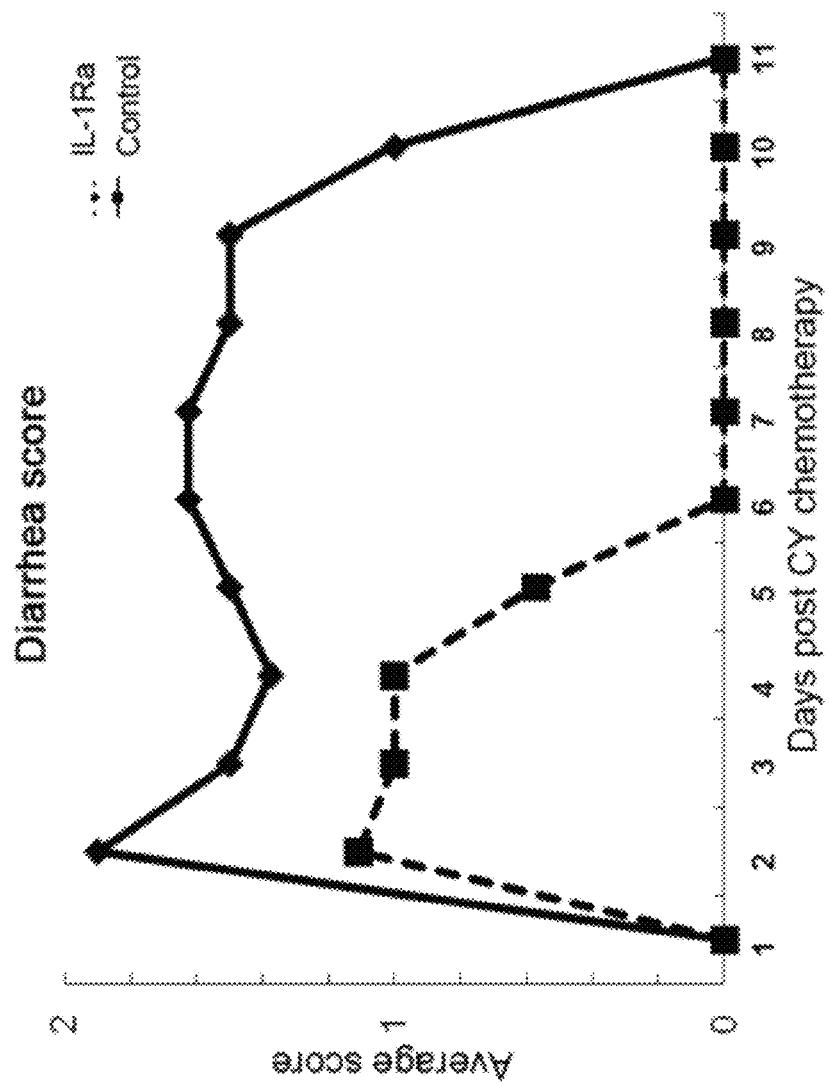
FIG. 18: The effect of IL-1Ra preventive plus therapeutic treatment on diarrhea score of the mice that received single dose cyclophosphamide chemotherapy.

Results: Diarrhea after single dose cyclophosphamide (550 mg/kg) chemotherapy. The severity of diarrhea in the rhIL-1Ra treated group was significantly lower than the control group (FIG. 18).

The mortality (10 mice per group) after single dose cyclophosphamide (550 mg/kg) chemotherapy.

Figure 19:
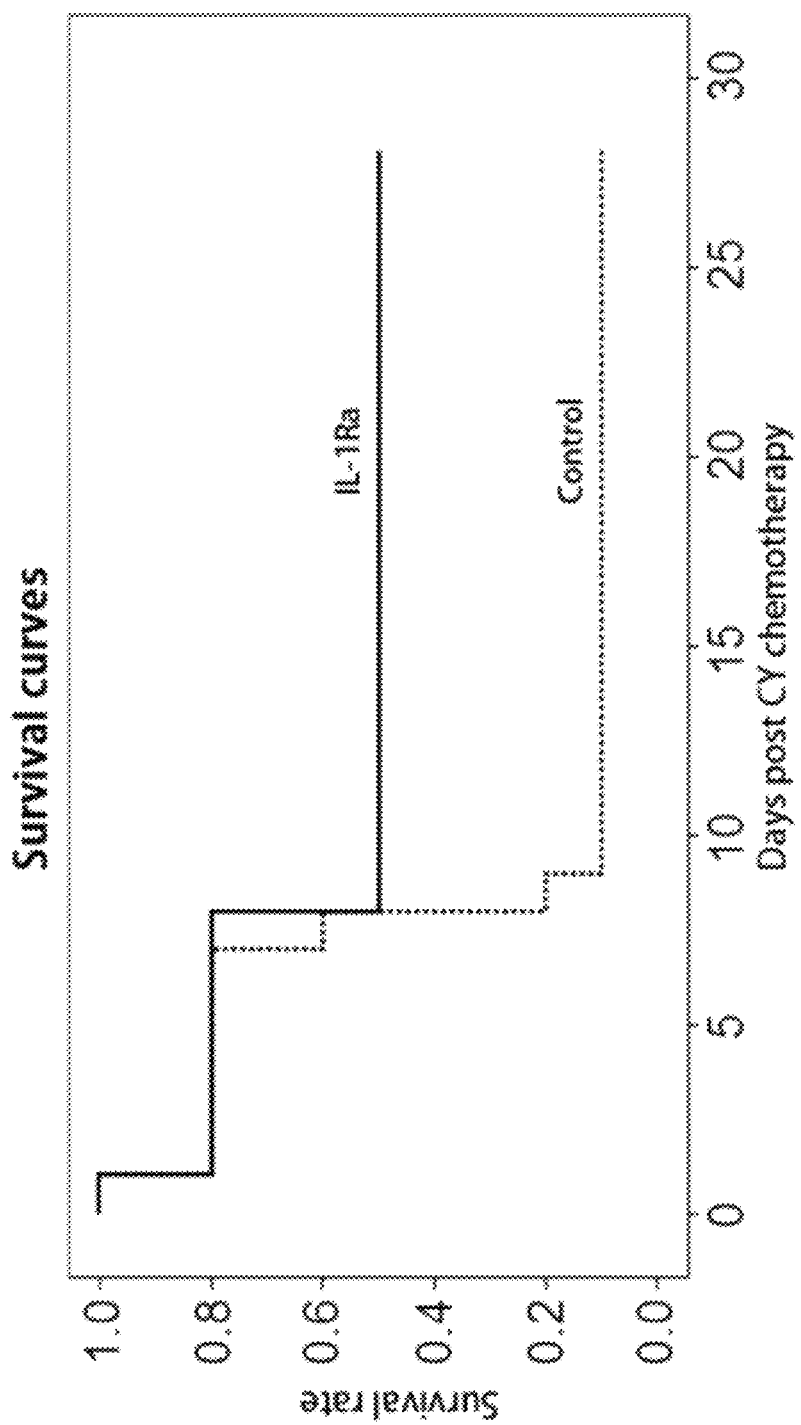
FIG. 19: The effect of IL-1Ra preventive plus therapeutic treatment on survival rate of the mice that received single dose cyclophosphamide chemotherapy.

The average survival time was 16.6 days in the rhIL-1Ra treated group, compared with 8.5 days in the control group. And the survival rate was increased from 10% of the control group to 50% in the rhIL-1Ra treated group (FIG. 19).

Example 9

The protective effect of IL-1Ra pretreatment on small intestine of chemotherapy treated mice. IL-1Ra pretreatment protects small intestine of the mice received single dose 5-fluorouracil (5-FU).

BALB/c mice (7 weeks old) were randomly divided into two groups, which were the PBS control group and recombinant mouse IL-1Ra (rmIL-1Ra) (amino acid sequence as shown in SEQ ID NO: 2) treated group. The rmIL-1Ra treated group was subcutaneously injected with 1 mg/kg/day rmIL-1Ra (77% homology with rhIL-1Ra) for 5 consecutive days (before injection, rmIL-1Ra was diluted to 100 μL by apyrogenic PBS at pH 7.4), and the control group was injected with 100 μL PBS at pH 7.4. At day 0, 5-FU (200 mg/kg) was administrated via tail vein injection. After three days of 5-FU injection, the mice were sacrificed and the villus length and crypt depth of their small intestine were examined.

Figure 21:
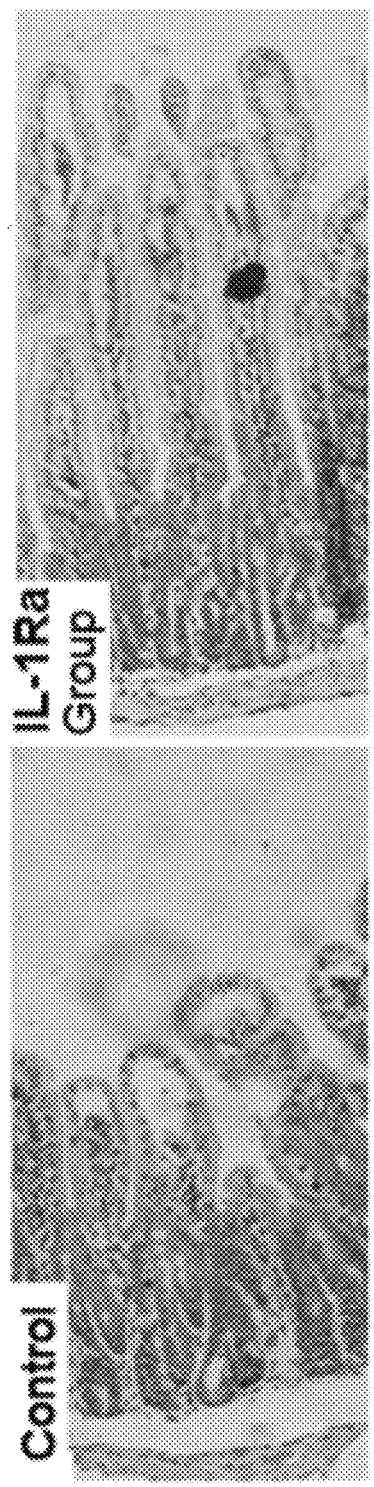
FIG. 21: Tissue sections shows the IL-1Ra protective effect on damaged intestine in the mice that received recombinant mouse IL-1Ra (rmIL-1Ra) (protein with SEQ ID NO: 2) for 5 consecutive days before 5-FU chemotherapy.
Figure 22:
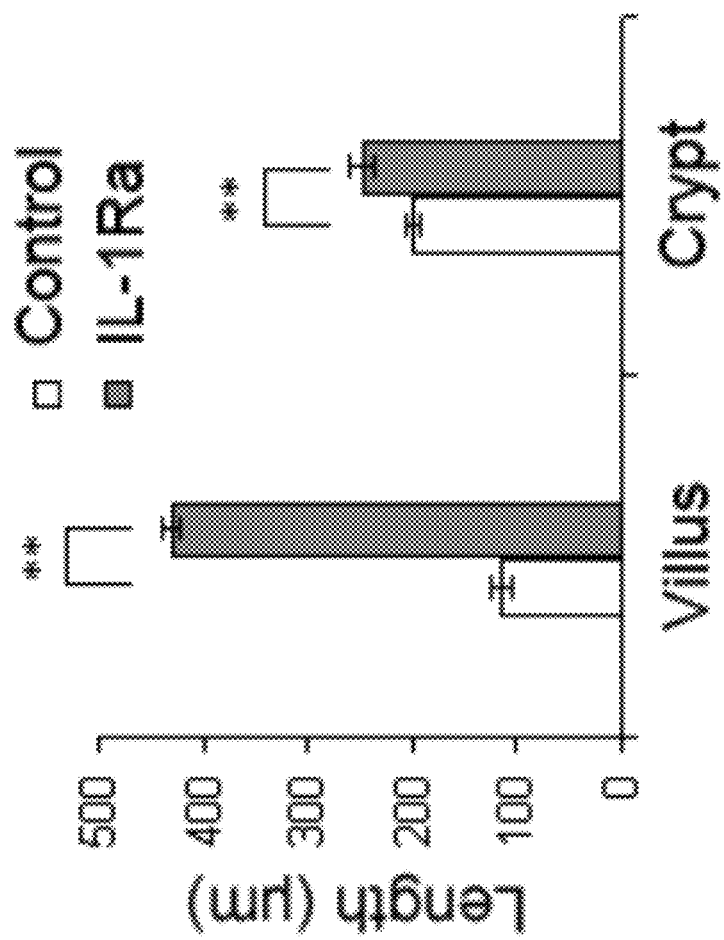
FIG. 22: The IL-1Ra protective effect on damaged intestine in the mice that received recombinant mouse IL-1Ra (rmIL-1Ra) (protein with SEQ ID NO: 2) for 5 consecutive days before 5-FU chemotherapy.

Results: Compared with the control group, the villus length and crypt depth of small intestine in the rmIL-1Ra treated group were significantly longer, which indicates that intestinal damage is reduced by rmIL-1Ra pretreatment (FIGS. 21, 22).

The present invention is not to be limited in terms of the particular embodiments described in this application, which are intended as single illustration of individual aspects of the invention. The scope of the invention also comprises other methods and compositions which have equivalent function. Actually, besides the content of the present invention, the technicians of this filed can easily carry out a variety of improvements to the invention according to above description and figures. Such improvements fall in the scope of the claims. The full text of each paper mentioned above is as reference for the present invention.

What is claimed is:

1. A method for treating chemotherapeutic agent-induced epithelium trauma of the intestinal mucosa in a subject in need thereof, comprising administering an effective amount of a protein selected from a group consisting of:

a. a protein having the amino acid sequence of SEQ ID NO: 1; or b. a protein having the amino acid sequence of SEQ ID NO: 2.

2. The method of claim 1, wherein the chemotherapeutic agent comprises an alkylating agent, antimetabolite, antibiotic, plant-derived anticancer agent, hormone, metal complex, or protein.

3. The method of claim 2, wherein the chemotherapeutic agent is cyclophosphamide or 5-fluorouracil.

4. The method of claim 1, wherein the intestinal mucosa is mucosa of the small intestine.

5. The method of claim 1, wherein the capacity to treat chemotherapeutic agent-induced epithelium trauma of the intestinal mucosa comprises the capacity to prevent the reduction of villus length, crypt length, crypt depth, or crypt width.

6. A method of ameliorating the symptoms of chemotherapeutic agent-induced epithelium trauma of the intestinal mucosa in a subject in need thereof, comprising administering an effective amount of a protein selected from a group consisting of:
   a. a protein having the amino acid sequence of SEQ ID NO: 1; or
   b. a protein having the amino acid sequence of SEQ ID NO: 2.

7. The method of claim 6, wherein the symptoms of chemotherapeutic agent-induced epithelium trauma of the intestinal mucosa comprise one or more of diarrhea, weight loss, and shortened survival.

\* \* \* \* \*

SEQUENCE LISTING

<160> NUMBER OF SEQ ID NOS: 2

<210> SEQ ID NO 1
<211> LENGTH: 152
<212> TYPE: PRT
<213> ORGANISM: Homo sapiens

```
<400> SEQUENCE: 1

Arg Pro Ser Gly Arg Lys Ser Lys Met Gln Ala Phe Arg Ile Trp
1               5                   10                  15

Asp Val Asn Gln Lys Thr Phe Tyr Leu Arg Asn Asn Gln Leu Val Ala
            20                  25                  30

Gly Tyr Leu Gln Gly Pro Asn Val Asn Leu Glu Glu Lys Ile Asp Val
        35                  40                  45

Val Pro Ile Glu Pro His Ala Leu Phe Leu Gly Ile His Gly Gly Lys
    50                  55                  60

Met Cys Leu Ser Cys Val Lys Ser Gly Asp Glu Thr Arg Leu Gln Leu
65                  70                  75                  80

Glu Ala Val Asn Ile Thr Asp Leu Ser Glu Asn Arg Lys Gln Asp Lys
                85                  90                  95

Arg Phe Ala Phe Ile Arg Ser Asp Ser Gly Pro Thr Thr Ser Phe Glu
            100                 105                 110

Ser Ala Ala Cys Pro Gly Trp Phe Leu Cys Thr Ala Met Glu Ala Asp
        115                 120                 125

Gln Pro Val Ser Leu Thr Asn Met Pro Asp Glu Gly Val Met Val Thr
    130                 135                 140

Lys Phe Tyr Phe Gln Glu Asp Glu
145                 150

<210> SEQ ID NO 2
<211> LENGTH: 152
<212> TYPE: PRT
<213> ORGANISM: Mus musculus

<400> SEQUENCE: 2

Arg Pro Ser Gly Lys Arg Pro Cys Lys Met Gln Ala Phe Arg Ile Trp
1               5                   10                  15

Asp Thr Asn Gln Lys Thr Phe Tyr Leu Arg Asn Asn Gln Leu Ile Ala
            20                  25                  30

Gly Tyr Leu Gln Gly Pro Asn Ile Lys Leu Glu Glu Lys Ile Asp Met
        35                  40                  45

Val Pro Ile Asp Leu His Ser Val Phe Leu Gly Ile His Gly Gly Lys
    50                  55                  60

Leu Cys Leu Ser Cys Ala Lys Ser Gly Asp Asp Ile Lys Leu Gln Leu
65                  70                  75                  80

Glu Glu Val Asn Ile Thr Asp Leu Ser Lys Asn Lys Glu Glu Asp Lys
                85                  90                  95

Arg Phe Thr Phe Ile Arg Ser Glu Lys Gly Pro Thr Thr Ser Phe Glu
            100                 105                 110

Ser Ala Ala Cys Pro Gly Trp Phe Leu Cys Thr Thr Leu Glu Ala Asp
        115                 120                 125

Arg Pro Val Ser Leu Thr Asn Thr Pro Glu Glu Pro Leu Ile Val Thr
    130                 135                 140

Lys Phe Tyr Phe Gln Glu Asp Gln
145                 150
```